(12) United States Patent
O'Keeffe et al.

(10) Patent No.: US 10,307,110 B2
(45) Date of Patent: Jun. 4, 2019

(54) SYSTEMS, DEVICES, AND METHODS FOR PERFORMING BREATHING EXERCISES, IMPROVING LUNG FUNCTION, PERFORMING PULMONARY MONITORING, AND/OR DETERMINING LUNG CAPACITY AND PEAK EXPIRATORY FLOW

(71) Applicant: Human Resolution Technologies, LLC, Boston, MA (US)

(72) Inventors: Gregory O'Keeffe, Boston, MA (US); Brian Dutton, Dracut, MA (US); Mark Seelig, Haverhill, MA (US); Debra Sarvis, Duxbury, MA (US); Raymond Cha, New York, NY (US)

(73) Assignee: Human Resolution Technologies, LLC, Boston, MA (US)

( * ) Notice: Subject to any disclaimer, the term of this patent is extended or adjusted under 35 U.S.C. 154(b) by 0 days.

(21) Appl. No.: 16/105,539

(22) Filed: Aug. 20, 2018

(65) Prior Publication Data

US 2019/0053769 A1 Feb. 21, 2019

Related U.S. Application Data

(60) Provisional application No. 62/547,809, filed on Aug. 19, 2017.

(51) Int. Cl.
*A61B 5/08* (2006.01)
*A61B 5/00* (2006.01)
(Continued)

(52) U.S. Cl.
CPC .......... *A61B 5/7278* (2013.01); *A61B 5/0803* (2013.01); *A61B 5/0871* (2013.01); *A61B 5/091* (2013.01); *A63B 23/185* (2013.01); *A63B 71/0622* (2013.01); *A61B 5/0002* (2013.01); *A61B 5/4836* (2013.01); *A61B 5/742* (2013.01); *A63B 2071/0625* (2013.01); *G10L 25/51* (2013.01)

(58) Field of Classification Search
CPC combination set(s) only.
See application file for complete search history.

(56) References Cited

U.S. PATENT DOCUMENTS 6,241,683 B1 * 6/2001 Macklem ............... A61B 5/091
600/529
9,138,167 B1 * 9/2015 Leydon .................. A61B 5/087
(Continued)

*Primary Examiner* — Eric J Messersmith
(74) *Attorney, Agent, or Firm* — Amy J. Embert; Hoge, Fenton, Jones & Appel, Inc.

(57) ABSTRACT

Systems, devices, and methods for determining a user's lung capacity may employ a sound-producing breathing device and a recording device such as a microphone included in a user electronic device (e.g., smart phone or tablet computer). A user may inhale or exhale through the sound-producing breathing device, thereby producing a sound that is received by the microphone and communicated to a processor. The processor may analyze the received sound recording to determine one or more sound intensity values over, for example, the duration of the received sound and/or points in time within the sound recording. The sound intensity values may then be used to determine the user's lung capacity.

18 Claims, 21 Drawing Sheets

701

(51) Int. Cl.
    *A61B 5/091*     (2006.01)
    *A61B 5/087*     (2006.01)
    *A63B 23/18*     (2006.01)
    *A63B 71/06*     (2006.01)
    *G10L 25/51*     (2013.01)

(56) References Cited

U.S. PATENT DOCUMENTS

| | | | | |
|---|---|---|---|---|
| 2015/0126888 | A1* | 5/2015 | Patel | A61B 5/087 |
| | | | | 600/538 |
| 2015/0216448 | A1* | 8/2015 | Lotan | A61B 5/6898 |
| | | | | 600/538 |
| 2016/0242701 | A1* | 8/2016 | Gonnen | A61B 5/7415 |
| 2017/0042503 | A1* | 2/2017 | Su | A61B 7/003 |
| 2017/0319106 | A1* | 11/2017 | Nassehi | A61B 5/6898 |

\* cited by examiner

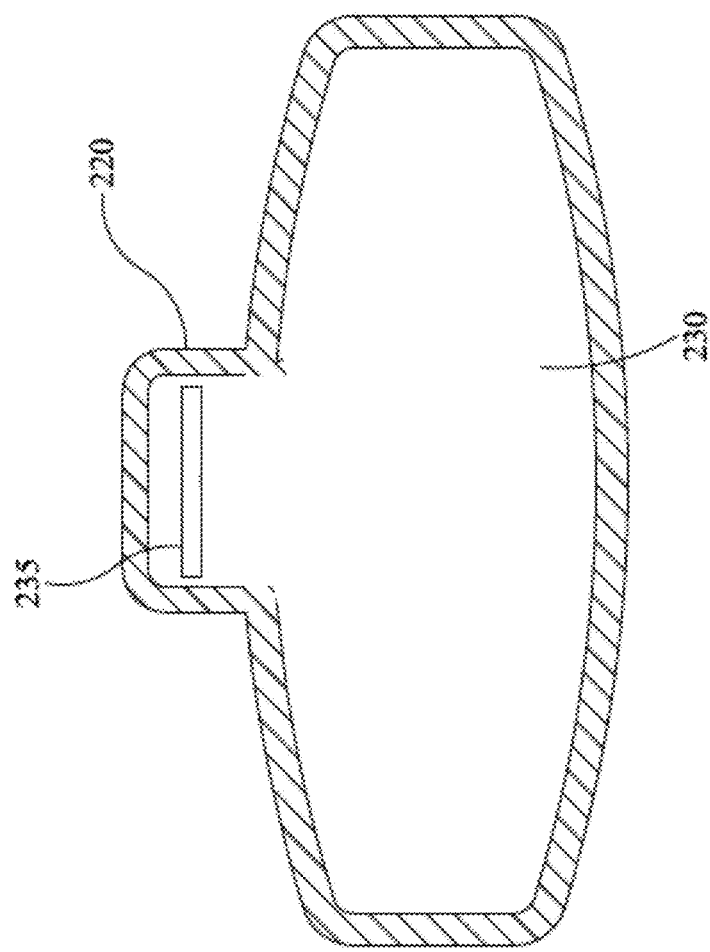

701

702

801

802

1005

User X Usage and Lung Function Report

View data for: Last week | Last Month | All Time

- Average Exhale Volume/Lung Capacity: 2L
  - (Goal: 2.2L)
- Peak Exhale Volume/Lung Capacity: 2.4L
- Average Exhale Volume/Lung Capacity: 2.1L
- Average Exhale Duration: 4.5s
- Peak Exhalation Flow Rate: 31 LPM
- Average Exhalation Flow Rate: 29 LPM

- Average Inhale Volume/Lung Capacity: 2.2L
  - (Goal: 2.2L)
- Peak Inhale Volume/Lung Capacity: 2.6L
- Average Inhale Volume/Lung Capacity: 2.3L
- Average Inhale Duration: 5.5s
- Peak Inhalation Flow Rate: 33 LPM
- Average Inhalation Flow Rate: 30 LPM

Average Number of Daily Uses: 14

FIG. 10E

SYSTEMS, DEVICES, AND METHODS FOR PERFORMING BREATHING EXERCISES, IMPROVING LUNG FUNCTION, PERFORMING PULMONARY MONITORING, AND/OR DETERMINING LUNG CAPACITY AND PEAK EXPIRATORY FLOW

RELATED APPLICATION

This application is a non-provisional of, and claims priority to, U.S. Provisional Patent Application No. 62/547,809 entitled "SYSTEMS, DEVICES AND METHODS FOR PERFORMING BREATHING EXERCISES" filed Aug. 19, 2017, which is incorporated by reference, in its entirety, herein.

FIELD OF INVENTION

The present invention is in the field of pulmonology and, more particularly, relates to systems, devices, and methods for performing breathing exercises and determining lung capacity and peak expiratory flow.

BACKGROUND

Performing breathing exercises and receiving feedback as to a volume of air inhaled or exhaled and analyzed to determine the lung capacity or respiratory function of a user typically requires the use of cumbersome and sometimes expensive equipment. Proper and regular use of traditional spirometry equipment is usually limited to clinical settings where patient engagement can be ensured under direct oversight. Once discharged, only a fraction of patients continue with their breathing exercises as instructed, exposing non-compliant patients to respiratory complications such as pneumonia.

SUMMARY

Systems, devices, and methods for determining a lung capacity and peak expiratory air flow of a user are disclosed herein. Exemplary systems include sound-producing breathing apparatus and a processor that is communicatively coupled to a microphone that may be resident within a user electronic device like a smart phone or tablet computer. The processor has a set of instructions stored thereon which when executed by the processor cause the processor to execute a method including receiving a recording of sound produced by a sound-producing breathing apparatus when a user inhales or exhales through the sound-producing breathing apparatus, the recording being made with a microphone resident within a user electronic device operated by the user. The microphone may be communicatively coupled to the processor. An intensity or frequency of the sound included in the received sound recording may then be determined. Then, a lung capacity of the user may be determined using the determined intensity and an indication of the lung capacity maybe provided to the user via, a display device included in the user electronic device. Exemplary user or electronic devices include, but are not limited to, smart phones and tablet computers. In some cases, the lung capacity may be communicated to a third-party computer system. At times, this method may include determining a peak air flow rate when the user is inhaling or exhaling when generating the sound captured in the sound recording.

In some embodiments, the sound recording is divided into a plurality of time intervals (e.g., 0.5 s, 0.1 s, etc.) and a sound intensity for each time interval may be determined. In these embodiments, lung capacity maybe determined by receiving a distance between the sound-producing breathing device and the microphone and accessing a correlation table stored in a database communicatively coupled to the processor. The correlation table may correlate sound intensity values (typically in dB) and air flow rates (typically in liters per minute (LPM) and may be specific to a distance between the sound-producing breathing device and the microphone and the type of sound-producing breathing device used to make the sound recording. Then, an air flow rate corresponding to the sound intensity for each time interval may be determined using the correlation table. A volume of air inhaled or exhaled for each time interval may then be determined and used to determine a total volume of air inhaled or exhaled for all the time intervals included in the plurality of time intervals of the sound recording. In some instances, a correlation table may not be available and may be generated by the processor.

At times, it may be determined whether the lung capacity falls below a threshold value and, if so, it may be determined whether an intervention is required and, if so, the intervention may be executed. In some embodiments, a goal for the user may be received and then it may be determined how the lung capacity compares to the goal and an indication of the comparison may be provided to the user.

In another embodiments, a lung capacity of a user may be determined by receiving a recording of sound produced by the sound-producing breathing apparatus when a user inhales or exhales through the sound-producing breathing apparatus, the recording being made with a microphone resident within a user electronic device operated by the user and communicatively coupled to the processor, determining a frequency of the sound included in the received sound recording, determining a lung capacity of the user based on the determined frequency, and facilitating provision of an indication of the lung capacity to the user.

In some instances, the sound recording may be divided into a plurality of time intervals and a sound frequency is determined for each time interval. In these instances, the determining of the lung capacity of the user also include accessing a correlation table stored in a database communicatively coupled to a processor. The correlation table may correlate sound frequency and air flow rates for the sound-producing breathing device. An air flow rate corresponding to the sound frequency for each time interval may be determined using the correlation table. Then, a volume of air inhaled or exhaled for each time interval may be determined and a total volume of air inhaled or exhaled for all the time intervals included in the plurality of time intervals. This total volume of air may correspond to the user's lung capacity. The correlation table may be specific to the type of sound-producing breathing device used to make the sound recording. At times, this method may include determining a peak air flow rate when the user is inhaling or exhaling when generating the sound captured in the sound recording and/or receiving a goal for the user, determining how the determined lung capacity compares to the goal, and providing of an indication of the comparison to the user.

BRIEF DESCRIPTION OF THE DRAWINGS

The present invention is illustrated by way of example, and not limitation, in the figures of the accompanying drawings in which:

FIG. 2C provides a cross-sectional view of the exemplary sound-producing breathing apparatus, consistent with some embodiments of the present invention;

FIG. 10E provides an exemplary user-monitoring portal interface, consistent with some embodiments of the present invention.

Figure 1:
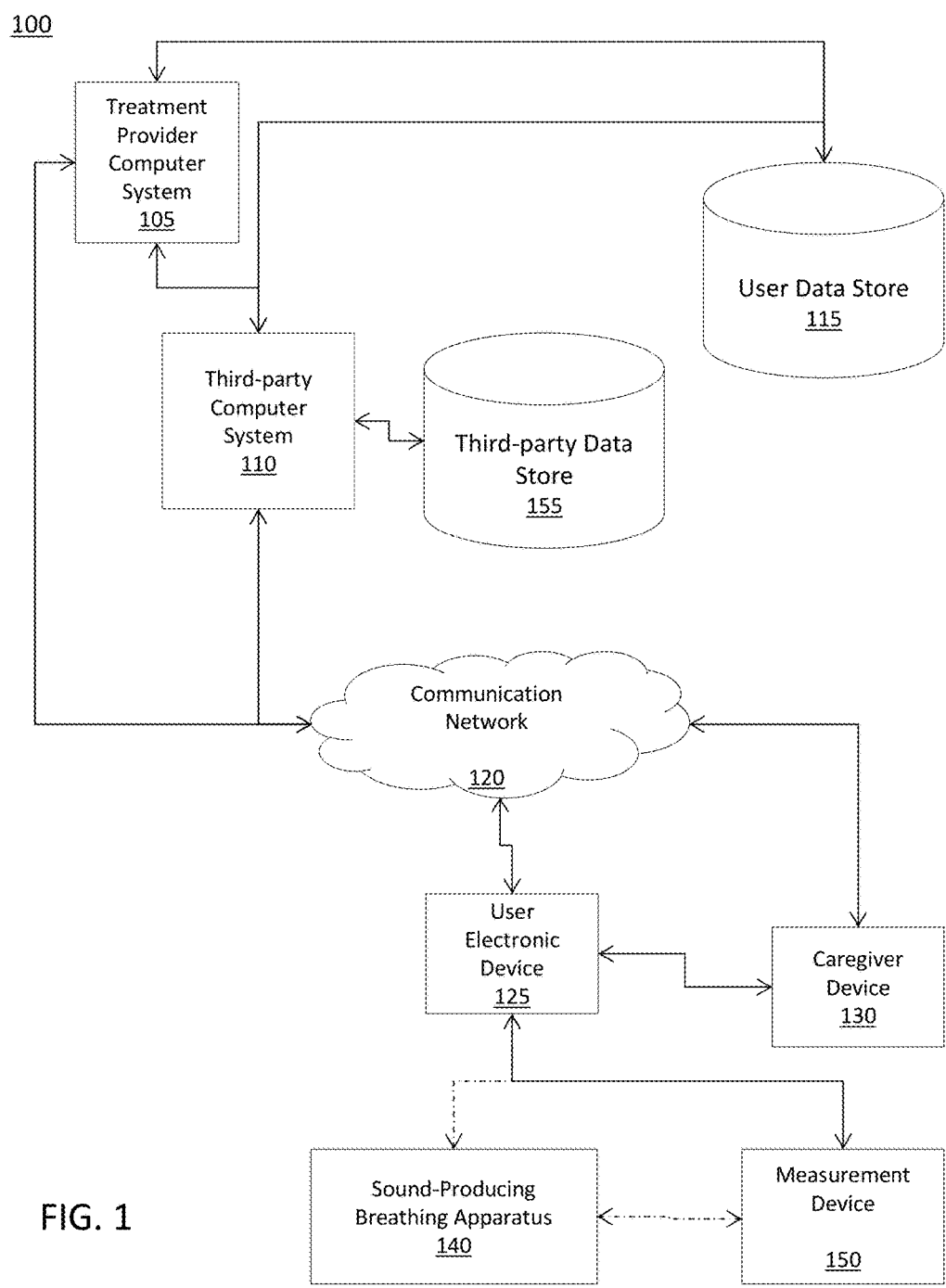
FIG. 1 is a block diagram of an exemplary system, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

WRITTEN DESCRIPTION

The present invention is related to systems, devices, and methods for performing breathing exercises to maintain or improve lung function, provide pulmonary monitoring, and/or determining a user's lung capacity or other pulmonary function. In many embodiments, the invention comprises a sound-producing breathing apparatus of known configuration that, when inhaled and/or exhaled through, produces a sound of a known frequency or range of frequencies. The sound produced by the sound-producing breathing apparatus is received and recorded by a microphone and communicated to a processor running a software program, or application that is configured to receive and analyze the recorded sound to for example, determine the user's lung capacity and/or state of health. The processor may be housed in an electronic device that may be a user's own user electronic device (e.g., smart phone or tablet computer) that may also include the microphone that received and recorded the sound.

In some embodiments, the invention may further comprise a back-end user-monitoring component that may, in some instances, be operated by, for example, a treatment provider (e.g., the user's physician, nurse, and/or medical aide) and/or a third-party healthcare monitoring service that may be in communication with a user's treatment provider(s) and/or hospital but may be a separate entity from the user's treatment provider(s) and/or hospital.

At times, the present invention may be in communication with one or more measurement devices, including, but not limited to, a pulse oximeter, a thermometer, and/or a blood pressure monitor that may wirelessly transmit measurements (e.g., blood oxygen level, heart rate, blood pressure, body temperature, etc.), or other readings regarding various bodily functions to the processor for processing by the software application via a wireless communication protocol such as Bluetooth.

A purpose of the invention disclosed herein is to aid in maintaining or improving lung capacity or function following, for example, a treatment or surgery that is typically performed in a hospital. For instance, the invention disclosed herein may be employed to monitor a user for a defined period of time (e.g., 30 or 90 days), or perpetually, following, for example, a diagnosis (e.g., cystic fibrosis (CF), chronic obstructive pulmonary disease (COPD), pneumonia, asthma or other diseases of the lungs), recovery from a treatment, or discharge from the hospital following a treatment or surgery (e.g., thoracic, joint replacement, etc.). In some instances, the invention may be used to perform pulmonary monitoring which may act to reduce preventable hospital admissions or readmissions for users with compromised respiratory systems by monitoring their lung capacity to detect potential problems.

In some instances, the invention disclosed herein may be used to monitor and/or calculate one or more aspects of the health or wellness (e.g., monitor lung capacity or lung function) of a healthy person (e.g., an individual who has not undergone a surgery or other medical intervention) such as an athlete or musician for the exemplary purpose of increasing lung capacity.

Another purpose of the invention is to reduce expenses related to medical care for users, healthcare providers, governmental agencies (e.g., Centers for Medicare and Medicaid Services (CMS)) and health insurance companies by, for example, early detection of lung conditions, other complications, and/or problems with a user's health or treatment recovery via monitoring of lung capacity.

FIG. 1 provides a block diagram of an exemplary system 100 that may be configured and/or used to implement one or more methods disclosed herein to, for example, conduct breathing exercises, improve user lung capacity, determine user lung capacity, determine a peak air flow rate for the inhalation and/or exhalation of a user, and perform pulmonary monitoring of a user. System 100 may include a treatment provider computer system 105, a third-party computer system 110, a user data store 115, a communication network 120, a user electronic device 125, a caregiver device 130, a sound-producing breathing apparatus 140, an optional measurement device 150, and a third-party data store 155. In some embodiments, the invention may be embodied in a system includes fewer components than system 100. For example, in some embodiments, system 100 may include only a user electronic device 125 and a sound-producing breathing apparatus 140 and, in other embodiments, system 100 may include only a user electronic device 125, third-party computer system 110, and sound-producing breathing apparatus 140.

In some instances, communication between two or more components of system 100 may be subject to one or more security protocols (e.g., encryption) to protect user-specific information and/or medically relevant information as may be required by, for example, HIPAA. Access to one or more components of system 100 may be limited by security protocols (e.g., passwords or identity verification protocols) designed to limit access to system 100 components to individuals who should access the component or components.

Treatment provider computer system 105 may be any computer system(s) associated with/operated by a treatment provider, including, but not limited to, physicians, surgeons, nurses, pharmacists, and administrative staff for a treatment provider as may be associated with, for example, a doctor's office or hospital. Third-party computer system 110 may be any computer system operated by a third party (i.e., not the treatment provider or patient/user). Exemplary third parties include, but are not limited to healthcare monitoring services. In some instances, treatment provider computer system 105 and third-party computer system 110 will be protected by a firewall and/or security protocols.

User data store 115 and/or third-party data store 155 may store information regarding users including, but not limited to, contact information, medical history of the user, pulmonary monitoring information, or pulmonary performance tests, any surgeries or medical procedures scheduled for the user, and previously determined lung capacity, peak air flows, and/or states of health. Additionally, or alternatively, user data store 115 and/or third-party data store 155 may store data regarding one or more user care protocols recommended and/or required by, for example, a hospital and/or treatment provider. In some cases, user data store 115 and/or third-party data store 155 may store lung, or pulmonary training instructions regarding how, when, and why to use system 100 or components thereof, goals for a user's lung capacity or pulmonary performance, and so on. Some or all of the data stored on user data store 115 and/or third-party data store 155 may be communicated to and/or stored on user electronic device 125 and/or measurement device 150.

Third-party computer system 110 may be a secure server, protected by one or more security protocols, to which only authorized individuals may have access privileges. Third-party computer system 110 may be configured to communicate with treatment provider computer system 105, third-party computer system 110, user data store 115, and/or third-party data store 155 to generate user care protocols, design pulmonary training regimes and/or testing specifications for one or more users according to, for example, one or more processes described herein.

Third-party computer system 110 may be configured to communicate a user care protocol, pulmonary training regimes, and/or pulmonary testing specifications to the user electronic device 125 via communication network 120 and receive one or more measurements, readings, and/or responses from user electronic device 125. Communication network 120 may be any network configured to facilitate communication between the components of system 100, such as the Internet or a mobile communication network.

User electronic device 125 may be any device configured to directly and/or indirectly communicate with third-party computer system 110 and/or a measurement device 150 and receive sound from sound-producing breathing apparatus 140. Exemplary user electronic devices 125 include smart phones and tablet computers. In many instances, user electronic device 125 will have a software application stored thereon adapted to execute in part, or in whole, the processes explained herein. This software application may be downloaded from, for example, the third-party computer system 110 and/or a server external to system 100. In some instances, the software application may be downloaded from a software marketplace such as the APPSTORE offered by Apple or the GOOGLE PLAY store offered by Alphabet. In some instances, the software application may be a secure (e.g., protected by encryption) mobile application configured to run on user electronic device 125 and may feature modular elements that can be easily adapted for different use cases and presentation of different user interfaces to a user to facilitate, for example, the user's use of system 100 and/or components thereof and understand testing or breathing exercise results.

In some embodiments, user electronic device 125 may be a device that was owned and/or operated by the user prior to receipt of user care protocol pulmonary training regimes, and/or pulmonary testing specifications from third-party computer system 110. This provides the advantage of a user electronic device 125 that the user has already purchased is already familiar with using. In some instances, user electronic device 125 may include one or more measurement devices including, but not limited to, a microphone, a camera, a proximity sensor, and/or a heart rate monitor.

Measurement device 150 may be configured to, for example, record sound produced by sound-producing breathing device 140 and/or take one or more physiological measurements of a user's lung capacity, pulmonary performance, oxygen saturation level, and/or health and, in some embodiments, system 100 may include more than one measurement device 150. Exemplary measurement devices 150 include a thermometer, blood pressure monitor, pulse oximeter, mobile ECG machine, blood glucose monitor, heart rate monitors, and camera. In some instances, a measurement device 150 may be enabled to take two or more types of measurements. For example, a heart rate monitor may also be able to monitor blood pressure. In many cases, a measurement device is configured to wirelessly communicate with user electronic device 125 via one or more wireless communication protocols (e.g., Bluetooth) but this need not be the case. For instance, measurement device 150 may be communicatively coupled to user electronic device 125 via a wire or other interface.

In one embodiment, measurement device 150 may be a telehealth tool (e.g., a computer or video conferencing system) that enables communication between the user and a caregiver and/or healthcare provider. Additionally, or alternatively, measurement device 150 may be a virtual reality system or audio/video presentation device.

In some instances, system 100 may include a device (not shown) that may be used to establish a known and/or constant distance between sound-producing breathing apparatus 140 and a microphone or receiver on the user electronic device 125. Exemplary devices that may be used to establish and/or maintain such a constant distance include, but are not limited to, a rigid attachment coupled to both the user electronic device 125 and sound-producing breathing apparatus 140; a bracelet, strap, or string tied affixed to both the user electronic device 125 and sound-producing breathing apparatus 140; and/or a sensor (e.g., a light (e.g., infra-red, near-infrared) sensor or ultrasonic sensor) or other devices (e.g., other tools included in the user electronic device 125 such as a camera or proximity sensor) of detecting the sound-producing breathing apparatus's 140 distance from the user electronic device 125, which may be operated by, for example, the software/mobile application running on the user electronic device 125.

In some instances, there may be two versions of the software/mobile application: one for the user (i.e., "the user version") by which the user may enter measurements of biometric data, answer questions regarding his or her recovery, set targets or goals, and/or view statistics, clinical feedback, or instructions and one for a caregiver(s) to keep track of the user's progress and needs and support or intervene as necessary. The software/mobile application may be a tool through which user data is collected and information is furnished to the user. The caregiver version of the application may be substantially similar to the user version of the software/mobile application; however, the caregiver may not be enabled to enter or access user data via the caregiver version of the application. Instead, the caregiver version of the application may provide an indication to the caregiver that the user has correctly entered the required data. In most cases, no user medical information is visible to the caregiver via the caregiver version of the application so as to, for example, protect the user's privacy.

In some embodiments, the present invention may further include a secure web application user-monitoring portal to which the readings received by the mobile application are transmitted via, for example, password-protected or otherwise encrypted protocols. Users of the web application may include, but are not limited to, users, caregivers, physicians, and other clinical staff and medical professionals who may be responsible for and/or interested in viewing, monitoring, editing and/or otherwise managing the user's care protocol. Access to the web application and/or features of the web application that a viewer may modify may be dependent on the viewer's relationship to the user or patient. For example, a viewer may not be able to modify a user care plan via the web application, but may be able to view all of the information entered into the web application and a caregiver (e.g., friend or spouse of the user or a patient who is a user) may only be able to access information regarding whether or not the breathing exercises were completed by the user in a timely manner and may have no further access to medically-sensitive or personally-identifying information.

These users may access the web application via, for example, third-party computer system 110. In some instances, the web application may further generate reports for users and/or clinicians, and/or caregivers using the data recorded (e.g., user frequency of usage, lung capacity volume measurements, changes in lung capacity, etc.). In some instances, the data collected may be used by the third party operating third-party computer system 110 to, for example, flag users when concerning measurements, determinations, and/or trends are observed so that they may, for example, establish communication with a user to, for example, assess the user's health and/or notify a treatment provider. In some instances, the collected data may be used by clinical staff to assist doctors and/or hospitals identify which users are in the greatest need of attention before reaching a physical state that requires a hospital admission or other medical intervention.

Sound-producing breathing apparatus 140 may be any device through which a user may breathe via his or her mouth, nose, or both and that produces a sound responsively to the air flow of the user's inhalation and/or exhalation. In some embodiments, the sound-producing breathing apparatus 140 may be a nose piece or a mask covering the nose and/or nose and mouth designed to encourage the user to breathe (e.g., inhale or exhale) using his or her nose rather than his or her mouth. In other embodiments, sound-producing breathing apparatus 140 may be a mouthpiece adapted for insertion into the user's mouth so that the user may breathe (e.g., inhale or exhale) using his or her mouth rather than his or her nose. An example of this embodiment of a sound-producing breathing apparatus 140 is shown in FIGS. 2A-2C, 4, and 7.

In some instances, sound-producing breathing apparatus 140 may be adapted/configured so that a first tone/sound, or set of tones/sounds, may be specific to inhaling air through the sound-producing breathing apparatus 140 and a second tone/sound, or set of tones/sounds, may be specific to exhaling through sound-producing breathing apparatus 140 so that tones/sounds, or set of tones/sounds made by inhaling may be distinguishable from tones/sounds, or set of tones/sounds made by exhaling. In some instances, sound-producing breathing device 140 may create a sound due to turbulent airflow produced by a pressure differential near a sound-producing mechanism (e.g., a reed or whistle-like opening) present in sound-producing breathing apparatus 140.

Sound-producing breathing apparatus 140 may be made from any appropriate material (e.g., plastic, metal, wood, and combinations thereof), may configured in any number of shapes and/or sizes, and may produce sound in one or a range of differing frequencies and/or intensities. In some instances, a sound-producing breathing apparatus 140 may be configured to generate a first tone or range of tones when the user is inhaling and a second tone or range of tones when the user is exhaling. Additionally, or alternatively, a first sound-producing breathing apparatus 140 may be configured so that it is harder to breathe through a second sound-producing breathing device 140 so that, for example, the user may increase, or decrease, the amount of resistance they encounter when inhaling or exhaling.

Figure 2A:
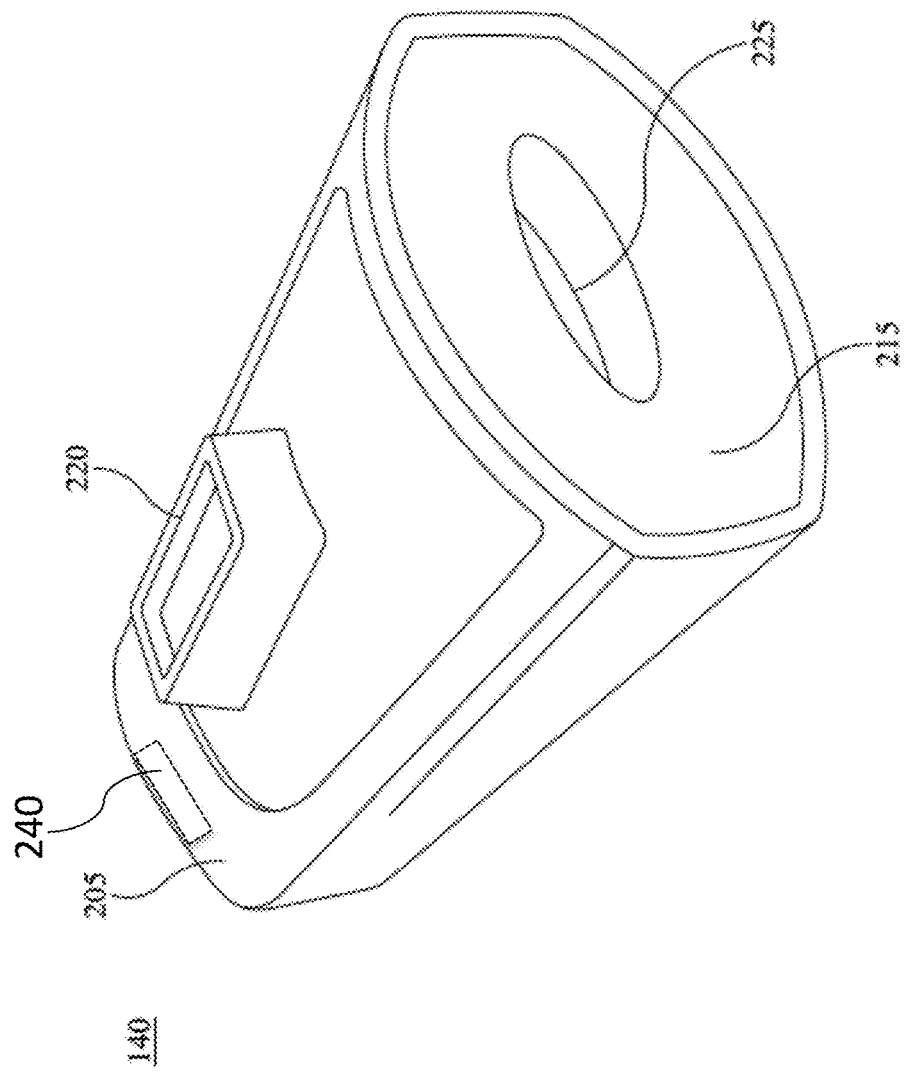
FIG. 2A is a front perspective view of an exemplary sound-producing breathing apparatus laying on its side, consistent with some embodiments of the present invention.
Figure 2B:
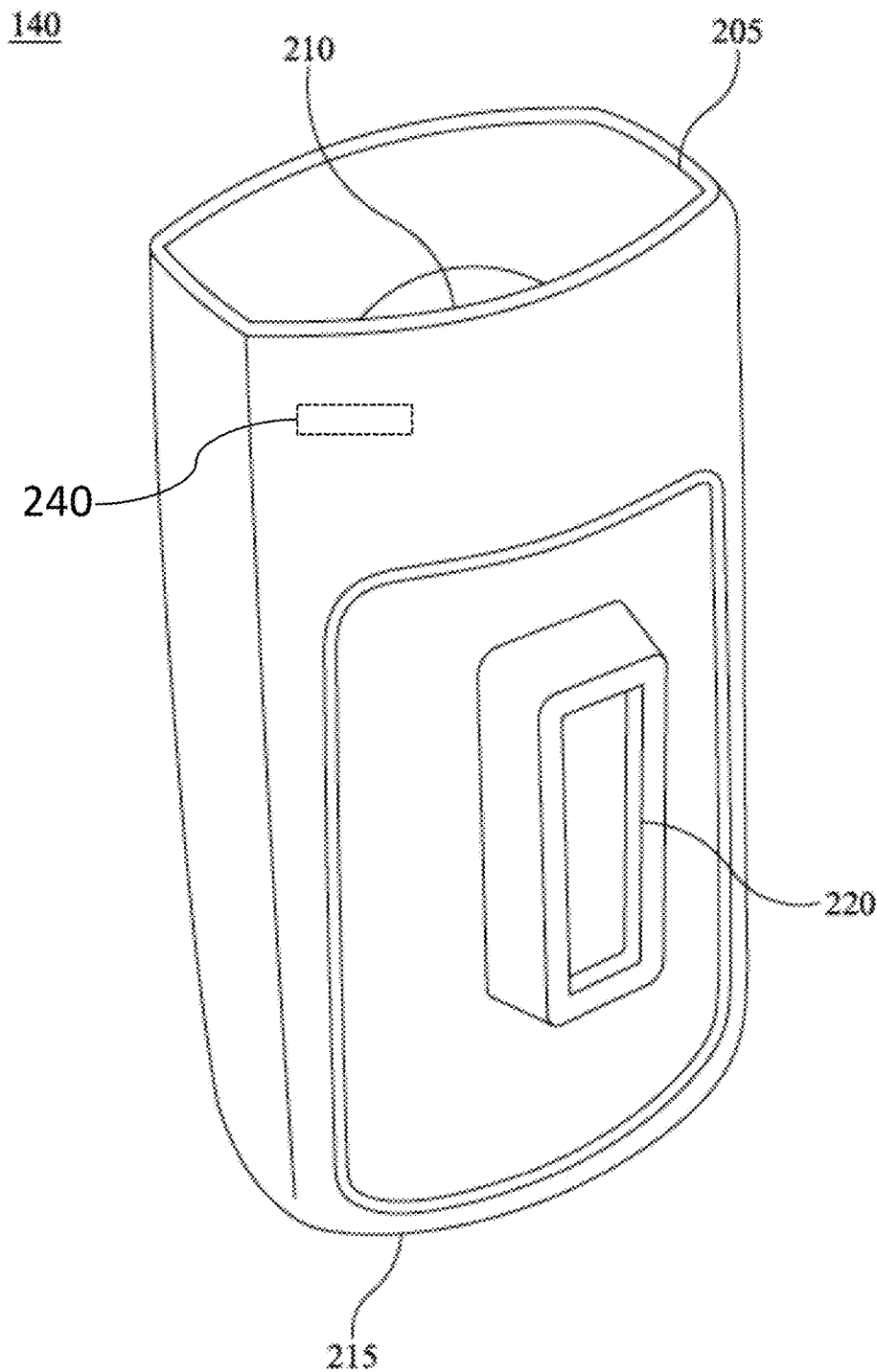
FIG. 2B is a perspective view of the exemplary sound-producing breathing apparatus when standing upright on an end, consistent with some embodiments of the present invention.

One exemplary sound-producing breathing device 140 is shown in FIGS. 2A-3C, where FIG. 2A provides a front perspective view of an exemplary sound-producing breathing apparatus 140 laying on its side, FIG. 2B provides a perspective view of the exemplary sound-producing breathing apparatus 140 when standing upright on an end, and FIG. 2C provides a cross-sectional view of the exemplary sound-producing breathing apparatus 140. The exemplary sound-producing breathing apparatus 140 of FIGS. 2A-2C includes a first end 205, a first orifice 210, a second end 215, a housing for a sound-producing mechanism 220, a second orifice 225, a tunnel 230, a sound-producing mechanism 235, and a proximity device 240. First end 205 is configured to face away from a user and towards a user electronic device 125 and/or measurement device 150 when in use. Second end 215 is configured to abut and/or be inserted into a mouth of the user so that the user may inhale air into first orifice 210, through tunnel 230, and into the user's mouth through second orifice 225. Housing 220 is positioned on sound-producing breathing apparatus 140 between first and second ends 205 and 215, respectively. In some embodiments, sound-producing mechanism 235 may be positioned within housing 220 proximate to tunnel 230 so that when air travels between the first and second orifices 210 and 225, respectively, the air flow contacts sound-producing mechanism 235, which produces a corresponding sound. Additionally, or alternatively, air may be pulled through an orifice in housing 220 and past sound-producing mechanism 235 thereby creating a sound. Air may be pulled through sound-producing mechanism 235 via, for example, an air pressure difference in tunnel 230 facilitated by the construction of sound-producing breathing device 140. Exemplary sound-producing mechanisms include, but are not limited to, reeds, paper, whistles, and the like.

In some embodiments, sound-producing breathing apparatus 140 may produce sound of different frequencies depending on a flow rate of air through the sound-producing breathing apparatus. For example, a sound-producing breathing apparatus 140 may be configured to produce sound that increases in frequency proportionally or disproportionally to an increase in a flow rate of air through the sound-producing breathing apparatus.

In some embodiments, the sound-producing mechanism may be configured to produce sound of a first known frequency, or first set of known frequencies, when in contact with air inhaled through first orifice 210 and produce sound of a second known frequency, or a second set of known frequencies, when in contact with air exhaled through the second orifice 225.

In many cases, the dimensions and features of the sound-producing breathing apparatus 140 and/or sound-producing mechanism 235 are consistent across units so that each one has the same proportions and dimensions and/or sound-producing mechanisms produce sound of a known. This enables the software/mobile application operating on the user electronic device to receive and analyze sound made by sound-producing breathing apparatus 140 when the user inhales or exhales such that the only variable in the system is the user's volume of air inhaled or exhaled over time.

Proximity device 240 may be any device that makes it easier for user electronic device 125 and/or measurement device 150 to determine a distance between the sound-producing breathing apparatus 140 and user electronic device 125 and/or measurement device 150. Exemplary proximity devices 240 include, but are not limited to, a transmitter of an electrical, light, or radio signal, a radio frequency identifier (RFID) chip, a visual marker (e.g., a dot, cross-hairs, or a target), and combinations thereof. When proximity device 240 is a visual identifier, a camera resident within user electronic device 125 and/or measurement device 150 may be configured to gage a distance between sound-producing breathing apparatus 140 and user electronic device 125 and/or measurement device 150 by determining a size of the proximity device 240 when imaged. When proximity device 240 transmits a signal, user electronic device 125 and/or measurement device 150 may be configured to receive the signal via, for example, communication interface 318, and determine a distance between sound-producing breathing apparatus 140 and user electronic device 125 and/or measurement device 150 by determining a property (e.g., strength, amount of spread, frequencies received, intensity, etc.) of the signal.

Exemplary sound-producing breathing apparatus 140 may be made of metal, plastic, or any other appropriate material (e.g., a composite or a combination of different materials). In some cases, a sound-producing breathing apparatus 140 may also have a handle and/or an adapter or attachment for coupling to the user electronic device (e.g., a port on the user electronic device such as a microphone jack).

The present invention may be used/practiced by, for example, users diagnosed with respiratory or pulmonary medical conditions and/or are recovering from a treatment and/or surgery that may impact their capacity to breath to, for example, track the user's pulmonary health or medical condition, lung capacity, blood oxygen levels, and/or overall health. In some situations, the present invention may be used by users who, for a variety of reasons, are bed-ridden to diagnose pneumonia or other respiratory conditions at an early stage so that they may be treated with minimum intervention and discomfort to the user.

In some cases, the present invention may be used to provide feedback to a user who is performing breathing exercises or is otherwise attempting to improve his or her breathing capacity. Exemplary uses for the present invention in non-medical contexts include those wishing to improve their breathing capacity such as swimmers, free divers, or athletes and/or those wishing to improve the evenness with which they inhale or exhale as may be useful to musicians who play, for example, wind instruments, or vocalists.

In many instances, the user will use his or her own user electronic device 125. This facilitates both ease of use (because the user is already familiar with how to use his or her device) and cost efficiency because the purchasing of a recording device or device that can provide access to a user account device is unnecessary.

Figure 3:
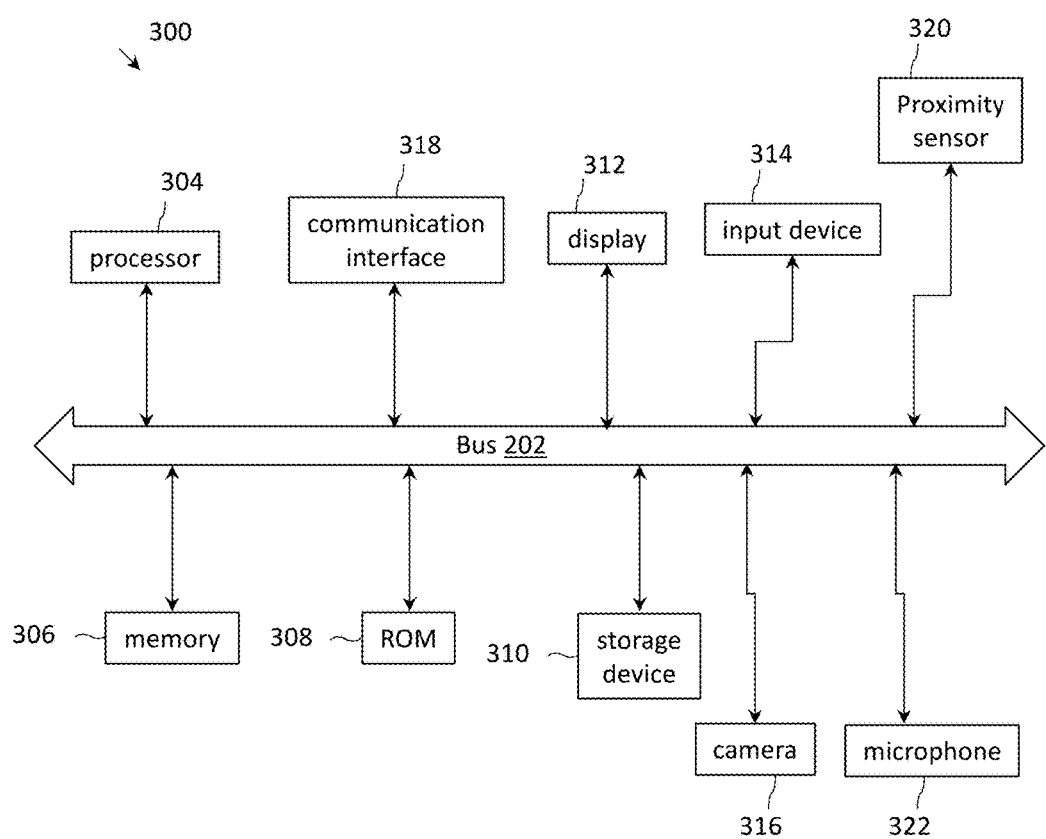
FIG. 3 is a block diagram showing exemplary components of a system in which computer readable instructions instantiating the methods of the present invention may be stored and executed, consistent with some embodiments of the present invention.

FIG. 3 provides an example of a system 300 that may be representative of any of the computing systems (e.g., user electronic device 125, measurement device 150, caregiver device 130) discussed herein. Examples of system 300 may include a smartphone, a desktop computer, a tablet computer, a laptop, an embedded system, etc. Note, not all of the various computer systems disclosed herein have all of the features of system 300. For example, certain ones of the computer systems discussed above may not include a display inasmuch as the display function may be provided by a client computer communicatively coupled to the computer system or a display function may be unnecessary. Such details are not critical to the present invention.

System 300 includes a bus 302 or other communication mechanism for communicating information, and a processor 304 coupled with the bus 302 for processing information. Computer system 300 also includes a main memory 306, such as a random access memory (RAM) or other dynamic storage device, coupled to the bus 302 for storing information and instructions to be executed by processor 304. Main memory 306 also may be used for storing temporary variables or other intermediate information during execution of instructions to be executed by processor 304. Computer system 300 further includes a read only memory (ROM) 308 or other static storage device coupled to the bus 302 for storing static information and instructions for the processor 304. A storage device 310, for example a hard disk, flash memory-based storage medium, or other storage medium from which processor 304 can read, is provided and coupled to the bus 302 for storing information and instructions (e.g., operating systems, applications programs and the like).

Computer system 300 may be coupled via the bus 302 to a display 312, such as a flat panel display, for displaying information to a computer user. An input device 314, such as a keyboard including alphanumeric and other keys, mouse, track pad, and/or a touch screen, may be coupled to the bus 302 for communicating information, command selections, directional information, gestures, and controlling cursor movement of/input by the user to the processor 304.

Computer system 300 may include a microphone 322 configured to receive sound, which may be recorded in, for example, memory 306, storage device 310, and/or ROM 308. Computer system 300 may further include a proximity sensor for determining when a user and/or sound-producing breathing device is proximate to the computer system and/or how close a user and/or sound-producing breathing device is to the computer system 300 and/or a component thereof (e.g., microphone 322). Other user interface devices, such as speakers, devices to cause vibrations, etc. are not shown in detail but may be involved with the receipt of user input and/or presentation of output.

The processes referred to herein may be implemented by processor 304 executing appropriate sequences of computer-readable instructions contained in main memory 306. Such instructions may be read into main memory 306 from another computer-readable medium, such as storage device 310, and execution of the sequences of instructions contained in the main memory 306 causes the processor 304 to perform the associated actions. In alternative embodiments, hard-wired circuitry or firmware-controlled processing units may be used in place of, or in combination with, processor 304 and its associated computer software instructions to implement the invention. The computer-readable instructions may be rendered in any computer language.

In general, all of the process descriptions provided herein are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 300 or similar electronic computing device, that manipulates and transforms data represented as physical (electronic) quantities within its registers and memories into other data similarly represented as physical quantities within its memories or registers or other such information storage, transmission or display devices.

Computer system 300 also includes a communication interface 318 coupled to the bus 302. Communication interface 318 may provide a two-way data communication channel with a computer network, which provides connectivity to and among the various computer systems discussed above. For example, communication interface 318 may be a local area network (LAN) card to provide a data communication connection to a compatible LAN, which itself is communicatively coupled to the Internet through one or more Internet service provider networks. The precise details of such communication paths are not critical to the present invention. What is important is that computer system 300 can send and receive messages and data through the communication interface 318 and, in that way, communicate with hosts accessible via the Internet. It is noted that the components of system 300 may be located in a single device or located in a plurality of physically and/or geographically distributed devices.

In some instances, one or more correlation tables as disclosed herein may be stored on user data store 115, third party data store 155, user electronic device 125, third-party computer system 110, treatment provider computer system 105, and/or measurement device 150. In other instances, the correlation tables and/or correlations included therein may be generated as-needed via, for example, use of one or more mathematical relationships, experimentally determined relationships, and/or algorithms by, for example, processor 304.

Figure 4:
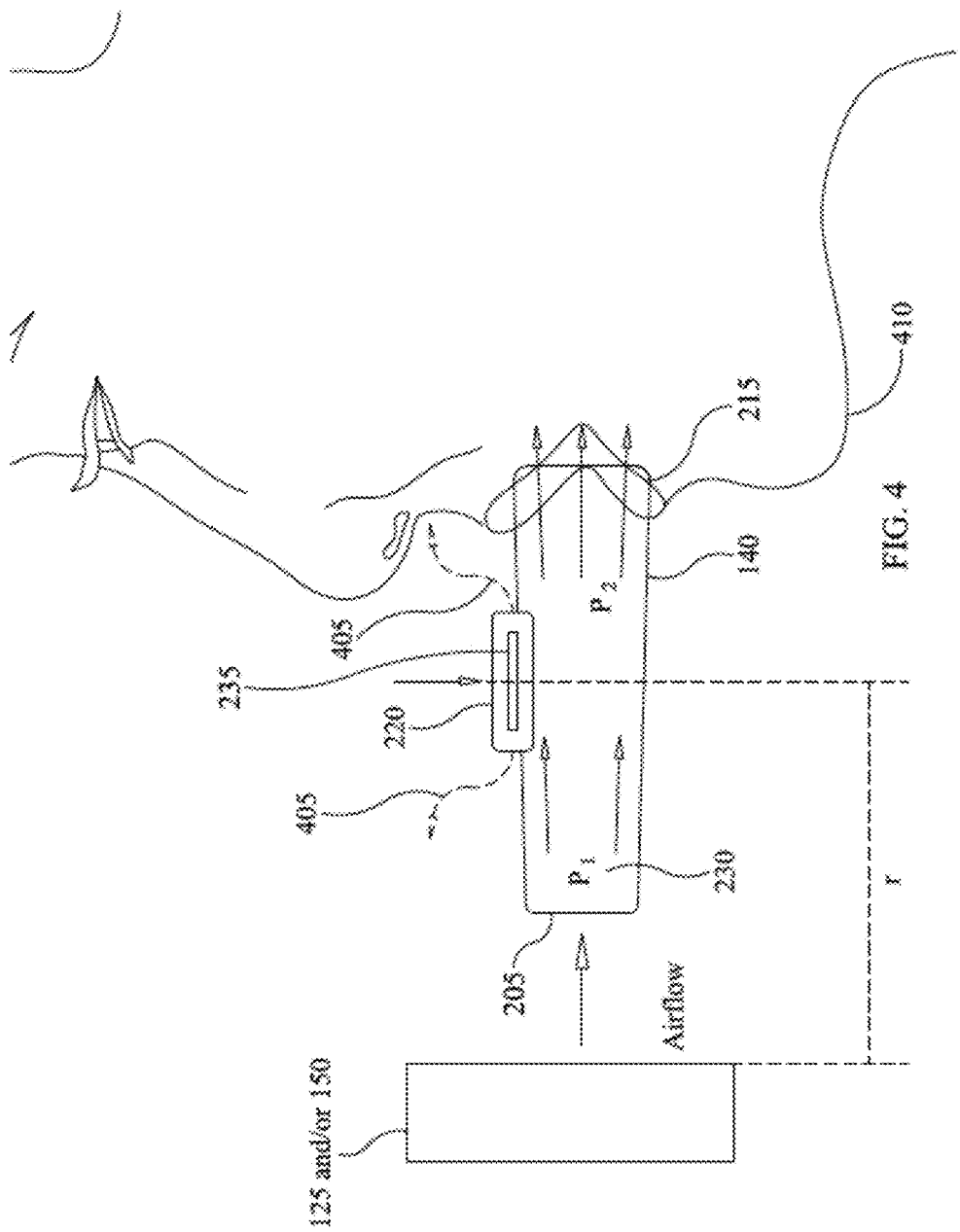
FIG. 4 is a diagram providing a longitudinal cross-section of an exemplary sound-producing breathing apparatus, consistent with some embodiments of the present invention.

FIG. 4 is a diagram providing a longitudinal cross-section of an exemplary sound-producing breathing device 140 that is shaped with a form factor similar to a kazoo where the user inhales through the larger end causing a pressure drop as the air travels from the narrow opening into a larger space below the reed, creating a low-pressure zone and turbulent airflow across the reed. More specifically, FIG. 4 shows how air may flow through tunnel 230 to produce or propagate sound that may be recorded by user electronic device 125 and/or measurement device 150. In the diagram of FIG. 4, second end 215 of sound-producing breathing device 140 is inserted into a user's mouth 410 (shown as an approximation) and the user is inhaling air through first end 205 into his or her mouth 410. The air flow created by the user's inhalation is shown in the diagram as solid lines with an arrow showing the direction of air flow. As air enters tunnel 230 through first end 205, it is of a first pressure $P_1$ and as the diameter of tunnel 230 increases along its length, the inhaled air is of a second pressure $P_2$. The configuration of sound-producing breathing device 140 is such second pressure $P_2$ is lower than first pressure $P_1$ (i.e., $P_1 > P_2$) and this drop in pressure acts to draw air into an opening in housing 220 and through sound-producing mechanism 235 into tunnel 230 and produce or propagate sound, shown in FIG. 4 as dashed lines 405. The sound propagates from sound-producing mechanism 235 in all directions and some of the sound is recorded by user electronic device 125 and/or measurement device 150.

A distance r between a microphone resident within user electronic device 125 and/or measurement device 150 and sound-producing mechanism 235 may be known and/or determined and may be used to determine an air flow rate though the sound-producing breathing apparatus 140 and approximate lung capacity discussed in further detail below with regard to FIGS. 5, 6, 7A-7C, and 8A-8C. When a values for r is not known, it may be, for example, entered by the user and/or determined via images taken using a camera, such as camera 216 and/or a proximity sensor such as proximity sensor 220 and/or determined via a proximity device 240 and/or communication between proximity device 240 and electronic device 125 and/or measurement device 150.

Figure 5:
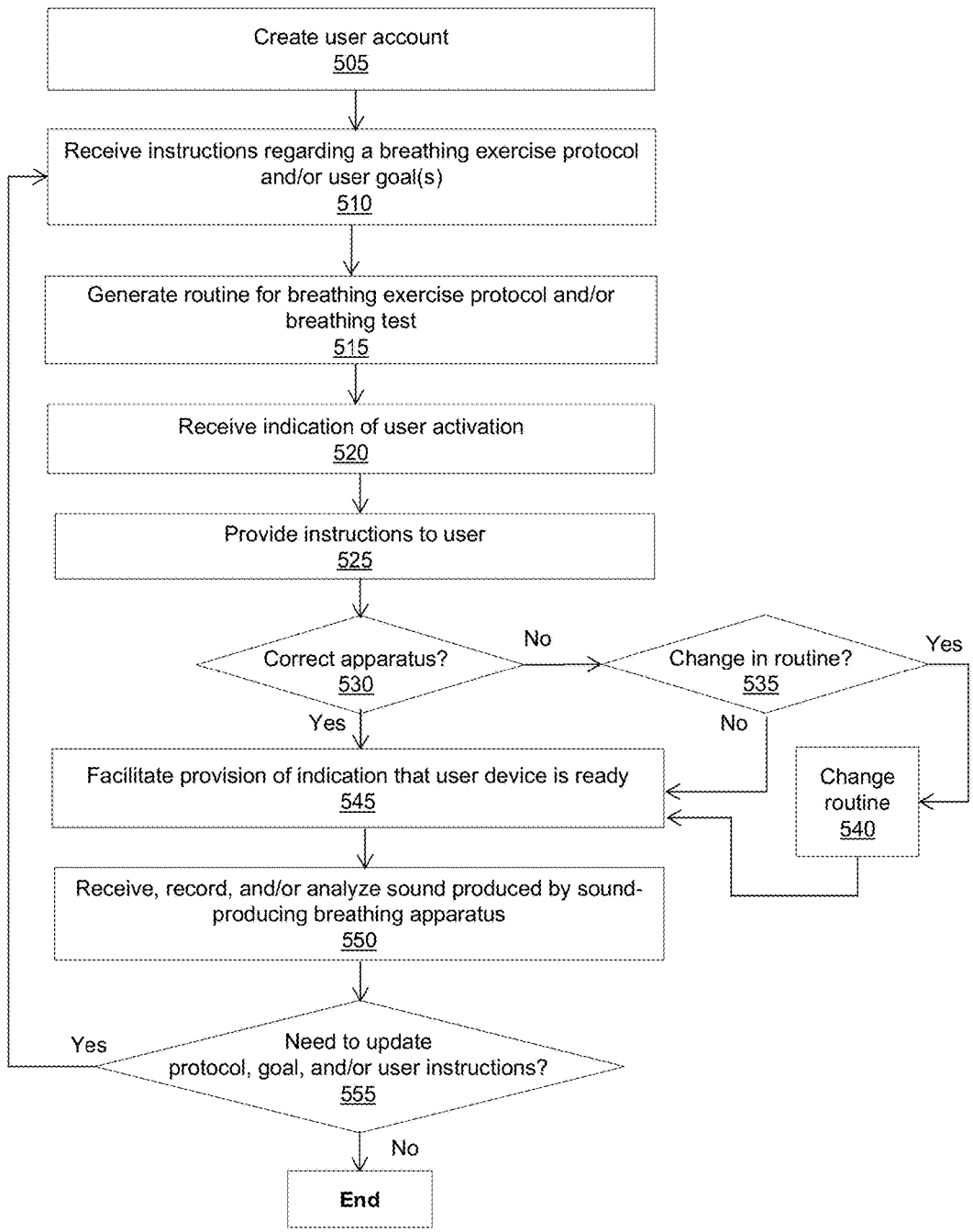
FIG. 5 is a flowchart illustrating an exemplary process for generation and/or updating of breathing exercise protocol, consistent with some embodiments of the present invention.

FIG. 5 is a flowchart illustrating an exemplary process 500 for generation and/or updating of breathing exercise protocol. Process 500 may be executed by a system like system 100 and/or a component or combination of components thereof. In some embodiments, process 500, or portions thereof, may be executed by a third-party service (i.e., not the user or user's physician) who monitors the user's lung/pulmonary health. This third-party service may provide monitoring information to, for example, a treatment provider and/or caregiver of the user on, for example, a continuous, as-needed/requested, and/or periodic basis via, for example, communication by third-party computer system 110 and/or third party data store 155 with treatment provider computer system 105.

Initially, a user account may be created (step 505). The user account may be created using, for example, treatment provider computer system 105, third-party computer system 110, and/or user electronic device 125. The user account may be embodied as a software application running on the user electronic device and often times, the user will interact with his or her user account via user electronic device 125.

The user account may be created at the request of, for example, the user and/or a physician or other treatment provider. In many cases, the user account and/or information associated therewith may be resident on and/or accessible by the user electronic device 125, treatment provider computer system 105, and/or third-party computer system 110. In some instances, information regarding the user (e.g., demographic information, information from an electronic medical record of the user (e.g., treatment information, diagnosis information, etc.)) may be associated with the user account (e.g., downloaded to user electronic device 125) via, for example, computer software and/or a website provided by, for example, the treatment provider and/or a third party operating third-party computer system 110. The created user account may be linked to and/or accessible by the user electronic device 125, the treatment provider computer system 105, and/or third-party computer system 110.

In step 510, instructions regarding a breathing exercise protocol and/or user goals regarding performance of the breathing exercises and/or breathing tests, and/or results thereof (e.g., breathing and/or lung capacity targets) may be received. The instructions may pertain to, for example, how the user is to use a sound-producing breathing apparatus to perform breathing exercises, a frequency of use, a duration of use, target volumes/intensities for produced sound, target durations for producing sound, features of a sound-producing breathing apparatus 140 (e.g., dimensions, brand name, type, etc.) to be used by the user. Optionally, updates to user instructions and/or goals may also be received in step 510 following an affirmative decision at step 555 as will be discussed in greater detail below.

In some instances, the received instructions may relate to treatment provider and/or treatment facility preferences (e.g., scheduling of breathing exercises, target durations and/or volumes/intensities of sound produced when using a sound-producing breathing apparatus 140, etc.) that may be consistent with a standard of care for a particular user or diagnosis associated with the user. These may be associated with the user account via active selection and/or by default.

Additionally, or alternatively, the received instructions may relate to user information (e.g., diagnosis, expected recovery times, age, etc.) and/or preferences (e.g., scheduling, reminder, and/or interface preferences).

Additionally, or alternatively, the received instructions may relate to equipment parameters of the sound-producing breathing apparatus (e.g., type, manufacturer, size, frequency range, volume or intensity range, etc.) and/or user device (e.g., type, brand, version, operating system, microphone capability, screen size, screen capability, etc.).

In step 515, a routine for a breathing exercise protocol and/or breathing test may be generated responsively to the instructions received in step 510, information associated with the user account, and/or default information (e.g., general instructions for use of a sound-producing breathing apparatus or performance of breathing exercises).

In some embodiments, generation of the routine in step 515 may include, but is not limited to, determining a schedule for when the user should engage in breathing exercises and/or tests, determining one or more parameters for the breathing exercises and/or tests, specifying parameters (e.g., target breathing duration, target sound intensities, number of repetitions of the breathing exercise to perform, etc.) of the breathing exercises and/or tests, and/or analysis of tones/sound received from the sound-producing breathing apparatus according to features and/or attributes of the sound-producing breathing apparatus.

Often times, execution step 515 may also include receiving information regarding features of the sound-producing breathing apparatus 140 and/or user electronic device 125 being used by the user. The protocol may be adapted, or otherwise adjusted, to optimize for different configurations of sound-producing breathing apparatuses and/or user devices, a distance between a particular sound-producing breathing apparatus and a particular user device, and/or treatment provider and/or user information/preferences as may be received in steps 505 and/or 510.

In step 520, an indication of an activation of the user account may be received. In some instances, the indication may be the user signing into his or her user account and/or opening or activating a software application running and/or associated with the user account on the user electronic device 125.

In step 525, instructions for conducting the breathing exercise routine and/or test may be provided to the user via his or her user electronic device. In many instances, the instructions will include directions for how to use the sound-producing breathing apparatus and where to position the sound-producing breathing apparatus relative to the user electronic device. In one instances, these instructions may include provision of a target on a user interface of the user electronic device that may be used in conjunction with a camera on the user electronic device such that the target is superimposed upon a video of the user when using the sound-producing breathing apparatus and the user electronic device. The target may inform the user where to position the user electronic device relative to the sound-producing breathing apparatus.

In some embodiments, the instructions provided in step 525 may include an instruction to sit down and sit up as straight as possible, place the sound-producing breathing apparatus 140 in his or her mouth, over his or her nose, or both (nose and mouth) and, in some cases, form a seal between sound-producing breathing apparatus 140 and the user's skin and/or lips. The user may be instructed to open the software/mobile application running/stored on his or her user electronic device, such as user electronic device 125 and position the open end of the sound-producing breathing apparatus toward the user electronic device. In some instances, the instructions may include a request to position the open end of the sound-producing breathing apparatus at a known, or fixed, distance from the user electronic device and/or measurement device, or a component thereof (e.g., a microphone like microphone 322). The user may then be instructed to breathe (i.e., inhale and/or exhale) as slowly and deeply as possible so that the sound-producing breathing apparatus begins, and continues to, make a sound.

On some occasions, execution of step 525 may include provision of a user interface to a user electronic device that may provide, for example, a visual display of a preferred, or target, range for an inhaled and/or exhaled air volume, a flow rate for inhaled and/or exhaled air, a volume or intensity of sound produced by a sound-producing breathing apparatus, a duration of sound production, and/or a type of sound (e.g., frequency or range of frequencies) to make using the sound-producing breathing apparatus. This user interface may also provide an indicator (e.g., a graph or number) showing where the user's inhalation/exhalation falls within the respective preferred or target range. In some instances, the user interface may further provide a goal for users regarding performing breathing exercises and a frequency (e.g., 2 times a day, 4 days a week, etc.) for doing so. Exemplary user interfaces are shown in FIGS. 9A-9E, which are discussed below.

In some instances, execution of step 525 may include instructing the user on how to use the sound-producing breathing apparatus and/or perform breathing exercises safely. In some cases, the instructions may tell the user to cough two or three times to clear secretions or congestion prior to beginning a breathing exercise or test and/or repeating them. Users who have an incision may be directed to support their incision while coughing by placing a pillow firmly against it.

In step 530, it may be determined whether the user is using the correct and/or a properly functioning sound-producing breathing apparatus. This may be executed by, for example, the user inputting the sound-producing breathing apparatus he or she intends to use into the user electronic device and/or performing a sound check using the sound-producing breathing apparatus. When the correct sound-producing breathing apparatus is not being used and/or when the sound-producing breathing apparatus is out of tune (i.e., producing undesired or unrecognized frequencies), then it may be further determined if a change in routine is desired (step 535) and/or if the breathing apparatus needs to be recalibrated. If so, then the routine may be changed to, for example, accommodate the different sound-producing breathing apparatus and/or may provide instructions regarding how to recalibrate the sound-producing breathing apparatus to the user, and/or adjustment of the routine and/or how the received sound is analyzed (step 540). This change may include, but is not limited to, adjustments to how lung capacity determinations are made using a received sound emanating from the sound-producing breathing apparatus when the user inhales and/or exhales through the sound-producing breathing apparatus. For example, if a breathing apparatus is out of tune, the change of step 540 may include updating how lung capacity determinations are made using the frequencies the sound-producing breathing apparatus is using.

When the correct sound-producing breathing apparatus is being used (step 530), no change in routine is necessary (step 535), and/or the routine is changed (step 540), provision of an indication that the user electronic device is ready to begin recording to the user inhaling or exhaling through the sound-producing breathing apparatus may be facilitated.

Then, in step of 550, a sound produced by the user when using the sound-producing breathing apparatus may be received, recorded, and/or analyzed. The receiving and recording of the sound is commonly executed by a user electronic device like user electronic device 125 and/or a measurement device 150 or a microphone (like microphone 322) included therein. The analysis may be done by the user electronic device and/or an external computer such as third-party computer system 110 and/or treatment provider computer system 105. The received/recorded sound may be analyzed to determine, for example, volume/intensity, duration, changes in tone, changes in volume/intensity, lung capacity, volume of air inhaled, volume of air exhaled, lung volume, blood oxygen level, and so on. In some instances, warbling or variations in the tone of the sound made by the user when using the sound-producing breathing apparatus may be used to assess for example, user health and/or lung capacity.

In some embodiments, performing the analysis of step 550 may include calculating one or more factors relating to how the sound is received by the user electronic device. For example, when the distance to the user electronic device is not known, or fixed (e.g., changes over the course of receiving the sound from the sound-producing breathing apparatus as may be measured by, for example an infrared sensor or camera included in the user electronic device), the distance of the sound-producing breathing apparatus from the user electronic device, measurement device, and/or microphone therein may be calculated using, for example, a flow rate of the sound and a volume/intensity, or decibel level, of the sound at the flow rate. In some embodiments, the user electronic device may include a camera and the user may be imaged and/or videotaped while performing the breathing exercises and/or tests. The images and/or video tape of the user may then be analyzed to determine if the user is moving when producing the sound and a determination regarding how that movement may impact features of the recorded sound.

Additionally, or alternatively, performing the analysis of step 550 may include processing the sound recording to isolate frequencies of interest or otherwise remove ambient noise not being made by the sound-producing breathing apparatus. This processing may include, but is not limited to, application of a filter to the sound recording to remove ambient noise, amplifying desired frequencies of the sound recording, using a lock-in amplifier to isolate desired frequencies of the sound recording, and so on.

Further details regarding the execution of step 550 are provided below with regard to process 600 shown in FIG. 6.

Then, in step 555, it may be determined whether the protocol, user goals and/or instructions may need to be updated responsively to, for example, the received, recorded and/or analyzed sound. If so, step 510 may be repeated and instructions to update the protocols, goals, and/or user instructions may be received. If not, process 500 may end.

Figure 6:
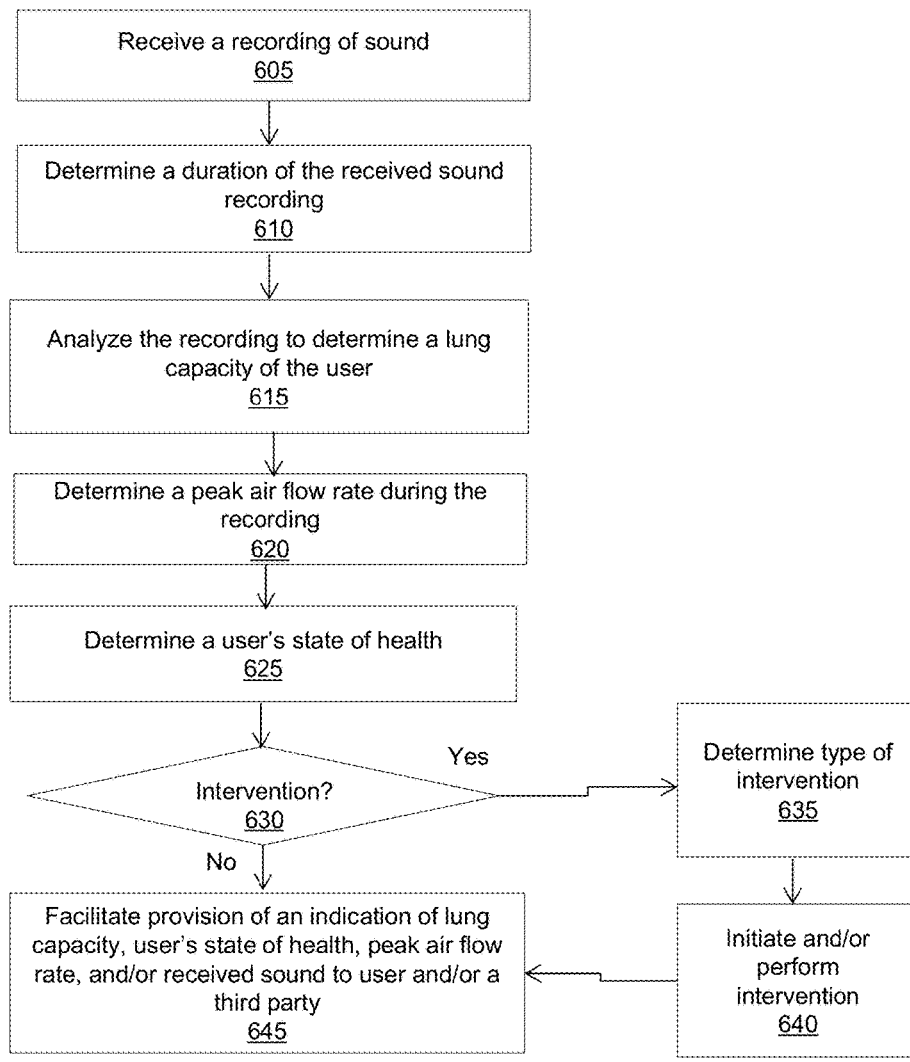
FIG. 6 is a flowchart depicting a process for determining a lung capacity of a user, peak air flow of inhalation and/or exhalation of a user, and/or a user's state of health, consistent with some embodiments of the present invention.

FIG. 6 is a flowchart depicting a process 600 for determining a lung capacity of a user, peak air flow rate of inhalation and/or exhalation of a user, and/or a user's state of health. Process 600 may be executed by a system like system 100 and/or a component or combination of components thereof. In some embodiments, process 600, or portions thereof, may be executed by a third-party service (i.e., not the user or user's physician) who monitors the user's lung/pulmonary health. This third-party service may provide monitoring information to, for example, a treatment provider and/or caregiver of the user on, for example, a continuous, as-needed/requested, and/or periodic basis via, for example, communication by third-party computer system 110 and/or third party data store 155 with treatment provider computer system 105.

Initially, a recording of sound made by a user using (e.g., inhaling or exhaling through) a sound-producing breathing apparatus like sound-producing breathing apparatus 140 over time may be received (step 605) by a processor, like processor 304, that may be resident in a user electronic device like user electronic device 125 and/or a measurement device like measurement device 150. The sound may be initially received and/or recorded by a microphone like microphone 322 in communication with the processor prior to execution of step 605. Optionally, in step 610, a duration of the sound recording may be determined by, for example, measuring a duration of the recording and/or how long the sound is of a particular frequency, volume, and/or intensity.

In step 615, the sound recording may be analyzed to determine a lung capacity of the user over, for example, the duration of the recording or portions thereof. Optionally, in some embodiments, the user's peak air flow rate during the sound recording for an inhalation and/or exhalation may be determined (step 620). In some embodiments, execution of step 615 may include processing the sound recording to isolate frequencies of interest or otherwise remove ambient noise not being made by the sound-producing breathing apparatus. This processing may include, but is not limited to, application of a filter to the sound recording to remove ambient noise, amplifying desired frequencies of the sound recording, using a lock-in amplifier to isolate desired frequencies of the sound recording, and so on.

Further details regarding how steps 615 and 620 may be executed are provided below regarding the discussions corresponding to FIGS. 7A-7C and 8A-8C.

Optionally, in step 625, the sound recording may be analyzed to determine a state of health and/or medical condition of the user. For example, if analysis of the recording indicates that the user cannot catch his or her breath, is coughing for a portion of the recording, is wheezing, or is making sounds that may indicate distress during the recording, then a determination that the state of the patient's health is problematic, sub-optimal, and/or worse than may be expected for the particular user may be made.

In some embodiments, audio of the user using the sound-producing breathing device may be continuously recorded throughout a breathing exercise session and that recording may be received in step 605 as opposed to a recording of only when the sound-producing breathing device is being used. In these embodiments, the received recording may be analyzed to determine periods of inhalation (i.e., when the tone the sound-producing breathing device produces when the user inhales is recorded), periods of exhalation (i.e., when the tone the sound-producing breathing device produces when the user exhales is recorded), sounds present between periods of inhalation and/or exhalation (e.g., coughing, wheezing, verbal comments, etc.) and these portions of the recording may be analyzed to determine a user's state of health and/or how he or she is feeling.

In step 630, it may be determined whether an intervention based on the user's lung capacity, peak air rate, and/or state of health is desired and/or required and, if so, in step 635 it may be determined what type of intervention is desired or required. Then, performance of the intervention may be initiated and/or performed (step 640). Interventions may be something relatively simple like a message provided to the user providing encouragement or follow-up instructions, a notification of an analysis result to the user's physician, etc. For example, data collected and/or determinations based thereon may be used to 'flag' or otherwise make a notation for the patient in his or her medical record or user account indicating that treatment provider follow up is desired or required. The treatment provider follow up could take the form of, for example, a phone call or office visit. In some cases, the intervention may involve using the onboard phone capabilities of the user electronic device to place a call to, for example, emergency services or a treatment provider. In some instances, the intervention may be the sending of a message via, for example, SMS or email to the user or the user's treatment provider.

When no intervention is required, or step 640 has been performed, provision of an indication of lung capacity, peak air flow rate, user's state of health, and/or receipt of the recorded sound to the user, a treatment provider, and/or a third party that may be operating third-party computer system may be facilitated (step 645).

Figure 7A:
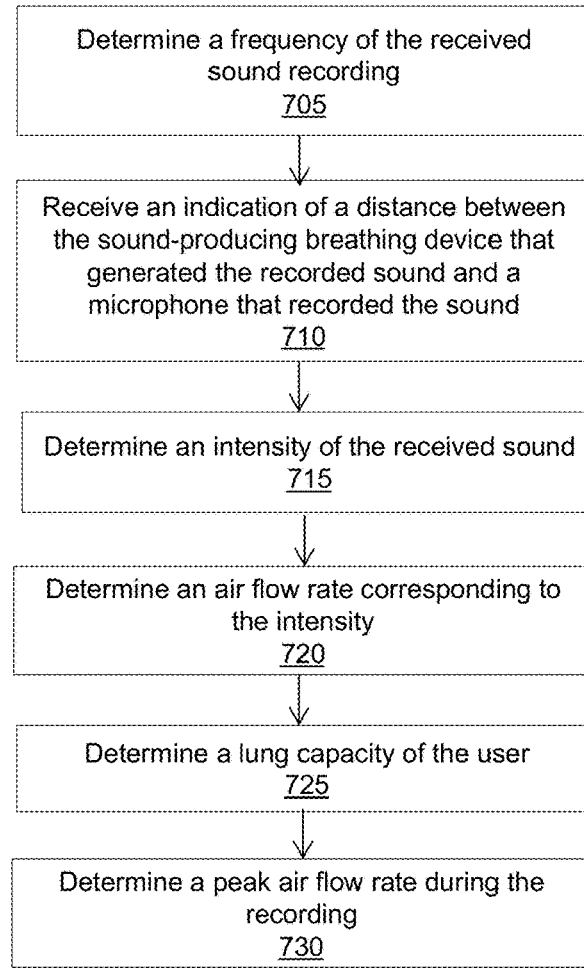
FIG. 7A is a flowchart depicting a process for determining a lung capacity of a user and/or a peak air flow rate of inhalation and/or exhalation of a user, consistent with some embodiments of the present invention.
Figure 7B:
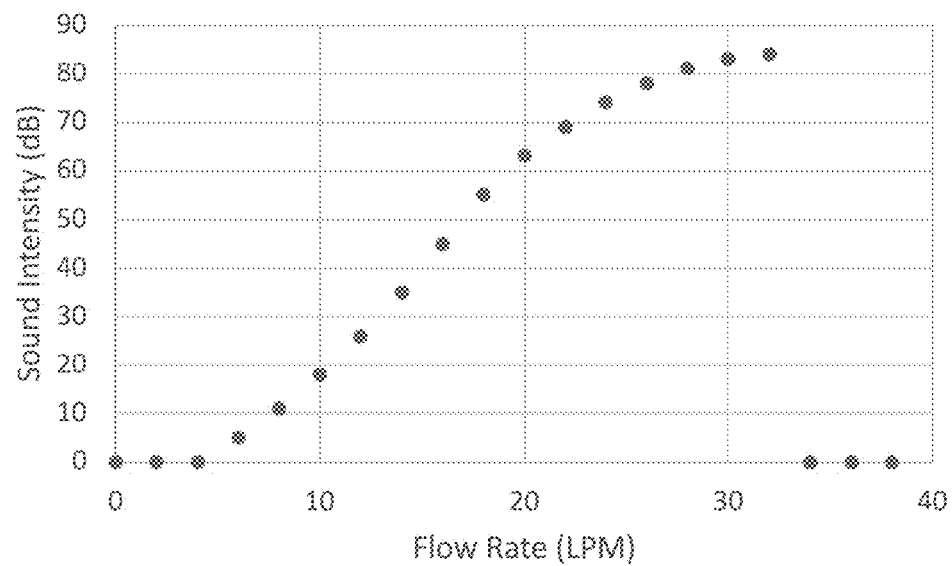
FIG. 7B depicts a graph plotting sound intensity as a function of air flow rate, consistent with some embodiments of the present invention.
Figure 7C:
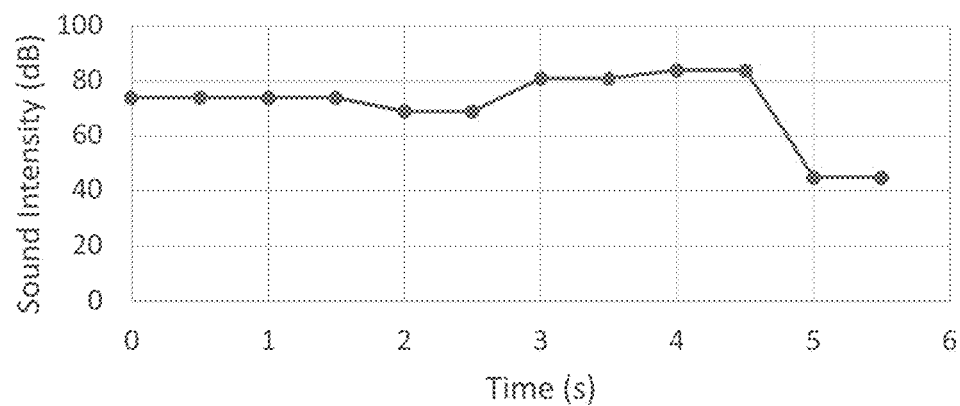
FIG. 7C depicts a graph plotting sound intensity as a function of time for a User X, consistent with some embodiments of the present invention.

FIG. 7A is a flowchart depicting a process 700 for executing step 615, determining a lung capacity of a user and/or a peak air flow rate of inhalation and/or exhalation of a user. Process 700 may be executed by a system like system 100 and/or a component or combination of components thereof.

Optionally, in step 705, a frequency of the sound recording may be determined. Step 705 may be performed when, for example, the user is using a sound-producing breathing device 140 that is configured to produce sound of a first frequency or first range of frequencies when the user is inhaling and a second frequency or second range of frequencies when the user is exhaling to determine whether the user is inhaling or exhaling. In instances where such a determination is not necessary, step 705 may be omitted from process 700.

In step 710, an indication of a distance between the sound-producing breathing device 140 that generated the recorded sound and the microphone that received/recorded the sound may be received. The distance may be received via, for example, direct entry of the distance by the user, use of an apparatus configured to maintain a consistent distance between the sound-producing apparatus and the microphone (e.g., a strap or stand), and/or a determination made by the user electronic device and/or measurement device via, for example, a camera like camera 216 and/or a proximity sensor like proximity sensor 220.

In step 715, an intensity, or volume, of the recorded sound may be determined. Typically, the sound intensity is determined in decibels (dB). The intensity of the recorded sound may be determined for specific intervals of time within the sound recording (e.g., every second or portion thereof (e.g., 0.1 seconds, 0.5 seconds, etc.)), averaged over the duration of the sound recording, and/or may be continuously determined throughout the sound recording. Then, and step 720, an air flow rate, usually determined in liters per minute (LPM) corresponding to the determined intensity may be determined. Step 720 may be executed by using a correlation table that correlates sound intensity with air flow rates. The correlations provided by such tables may be experimentally determined based on the sound-producing breathing device being used and the distance between the sound-producing breathing device and the microphone and multiple correlation tables may be generated and/or available wherein each correlation table is specific to 1) a type of sound-producing breathing device used and 2) a distance between the sound-producing breathing device and the microphone. An example of a correlation table that correlates intensity with air flow rates for a sound-producing breathing device positioned 30 cm from the microphone (i.e., $r=30$ cm) is provided in Table 1, reproduced below.

TABLE 1

| Flow Rate (LPM) | Sound Intensity (dB) |
|---|---|
| 0 | 0 |
| 2 | 0 |
| 4 | 0 |
| 6 | 5 |
| 8 | 11 |
| 10 | 18 |
| 12 | 26 |
| 14 | 35 |
| 16 | 45 |
| 18 | 55 |
| 20 | 63 |
| 22 | 69 |
| 24 | 74 |
| 26 | 78 |
| 28 | 81 |
| 30 | 83 |

TABLE 1-continued

| Flow Rate (LPM) | Sound Intensity (dB) |
|---|---|
| 32 | 84 |
| 34 | 0 |
| 36 | 0 |
| 38 | 0 |
| 40 | 0 |

The values of Table 1 indicate that a flow rate of at least 6 LPM per minute is required to produce a sound using the sound-producing breathing device used to generate the data provided by Table 1 and that when the flow rate is 34 LPM, or higher, the sound-producing breathing device does not make a relevant sound. A graph 701 showing the sound intensity (dB) values of Table 1 plotted against the flow rate (LPM) of Table 1 is provided in FIG. 7B.

In some instances, a correlation table specific to a particular sound-producing breathing device and distance (r) may not be available and, in these instances, the correlations of sound intensity and air flow rates may need to be determined and/or approximated using, for example, the inverse square law (reproduced below as Equation 1) and/or other equations describing fluid dynamics or aeroacoustics (e.g., the perfect gas equation of state, Navier-Stokes equations, etc.).

$$P/4\pi r^2 = I \quad \text{Equation 1}$$

Where:
P=sound power
r=a distance between the sound-producing breathing device and the microphone; and
I=recorded sound intensity.

The distance indication received in step 710 and the determined intensity of the sound (from step 715) may be input as r and I, respectively, in Equation 1 to determine a sound power for the recording and/or a time interval of the recording. This sound power determination may then be compared with experientially known correlations between sound power and air flow rates to determine the user's lung capacity. In some instances, these correlations may be specific to a particular type of sound-producing breathing device 140.

Figure 9A:
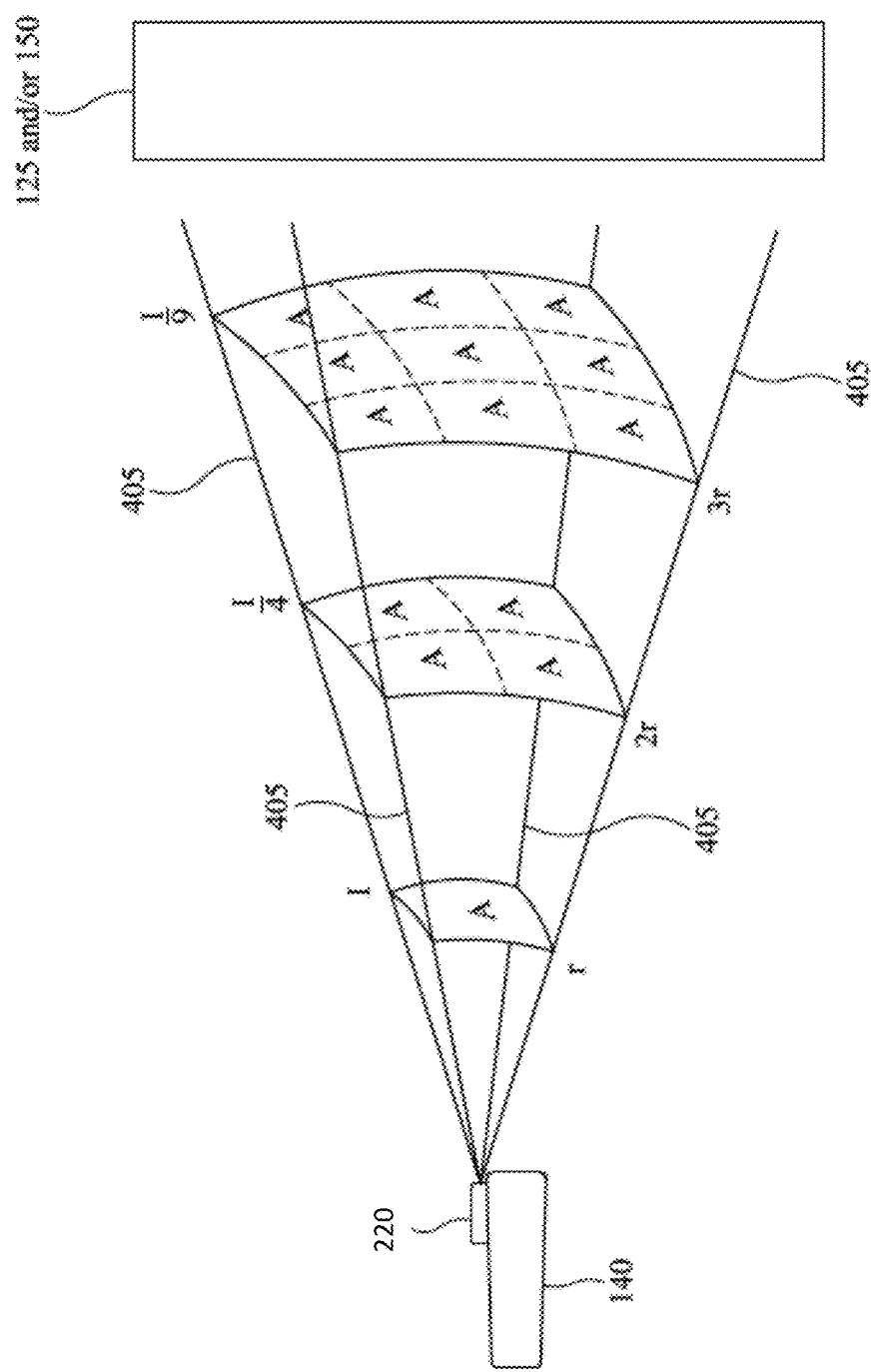
FIG. 9A provides a diagram of showing how sound intensity decreases with a distance from a point source of sound, consistent with some embodiments of the present invention.

FIG. 9A provides a diagram of showing how sound intensity (I) decreases with a distance between the sound-producing breathing device 140/housing 220 and the user electronic device and/or measurement device. In the diagram of FIG. 9A, representations of sound propagating from housing 220 are shown as lines 405 that spread out as they travel a distance r, 2r, 3r, etc. The intensity (I) of the sound is decreased according to the inverse square law (i.e., Equation 1) so that an intensity at a distance r is represented as "I," an intensity at a distance of 2r is ¼ as intense, which is represented as I/4 on the diagram and an intensity at a distance of 3r is ⅑ as intense, which is represented as I/9 on the diagram.

Figure 9B:
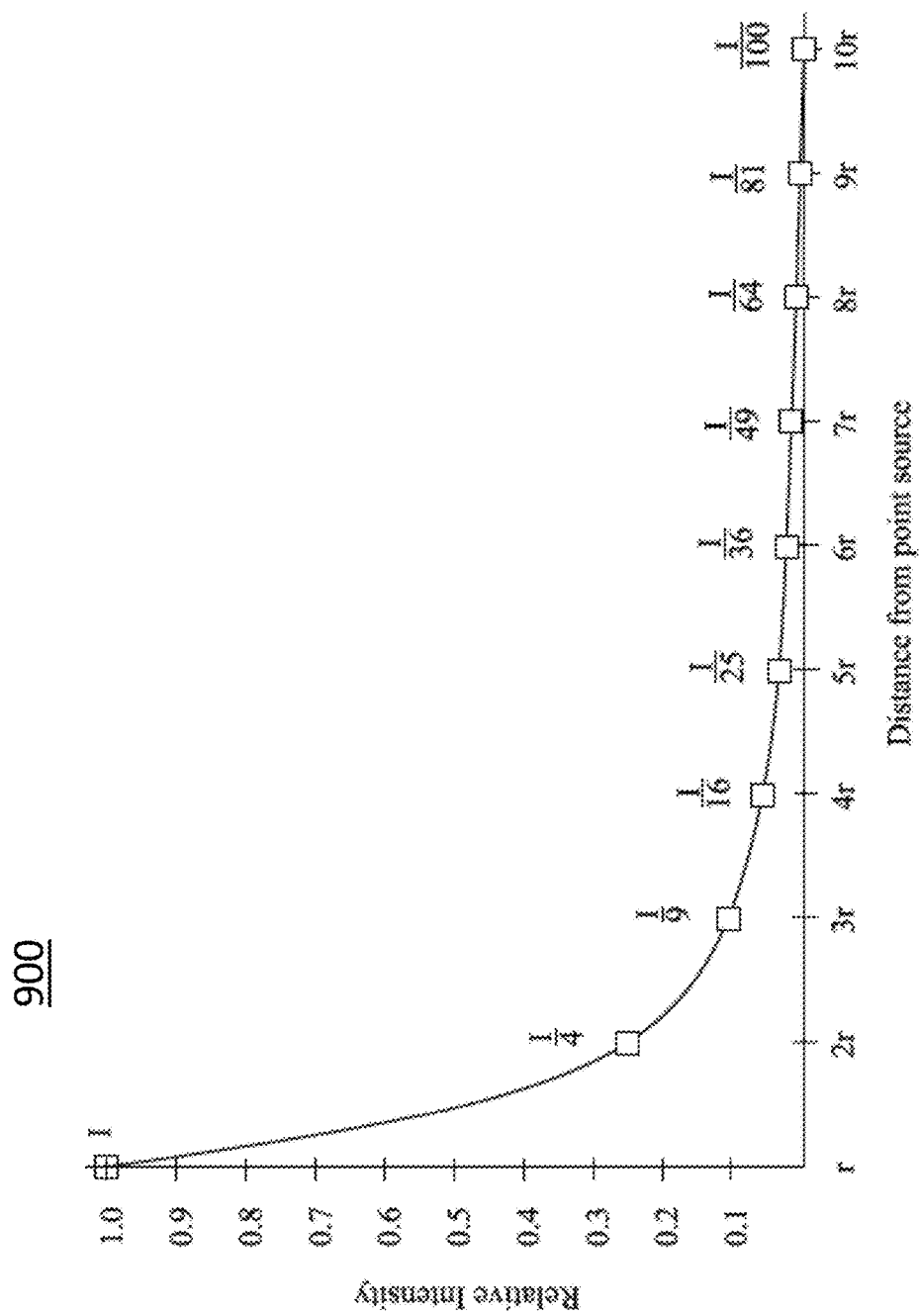
FIG. 9B shows a graph of relative sound intensity as a function of distance from a point source of sound, consistent with some embodiments of the present invention.

FIG. 9B shows a graph of relative sound intensity as a function of distance of a recording device (e.g., user electronic device 125, measurement device 150, and/or microphone 322) from a point source of sound, such as sound-producing breathing device 140 and/or housing 220. The graph demonstrates that intensity exponentially decreases as distance from a point source of a sound increases. For example, at a distance between a point source and a recording device of r, the relative sound intensity has a value of I, when a distance between the point source and the recording device is 2r, the relative sound intensity has a value of ¼ I, or (I/4), when a distance between the point source and the recording device is 3r, the relative sound intensity has a value of ⅑ I, or (I/9) and so on.

Then, in step 725, a lung capacity, in liters of air, of the user may be determined. The lung capacity of the user may be determined by, for example, using the flow rate and the duration of the sound recording and/or a portion of the sound recording used to determine the flow rate for that portion of the recording.

Table 2 provides data for an exemplary sound recording of a user (referred to herein as User X) as may be received in step 605, which shows time in seconds (s) and sound intensity in dB. The sound recording was made by a user using the sound-producing breathing device used to make correlation Table 1 at a distance of 30 cm from the microphone. The overall duration of the sound recording of Table 2 is 5.5 seconds and determinations of sound intensity are made every 0.5 seconds.

TABLE 2

| Time (s) | Sound Intensity (dB) |
|---|---|
| 0 | 74 |
| 0.5 | 74 |
| 1 | 74 |
| 1.5 | 74 |
| 2 | 69 |
| 2.5 | 69 |
| 3 | 81 |
| 3.5 | 81 |
| 4 | 84 |
| 4.5 | 84 |
| 5 | 45 |
| 5.5 | 45 |

A graph 702 showing the sound intensity (dB) values of Table 2 plotted against the flow rate (LPM) of Table 2 is provided in FIG. 9. The data of Tables 1 and 2 may then be combined (as show in Table 3, below) to determine a volume of air inhaled or exhaled for each interval of time (i.e., 0.5 s) and these determined values may be added together to determine a total volume of air combined, or lung capacity. Stated differently, a volume of air inhaled or exhaled by the user using the sound-producing breathing device may be determined by calculating the area under a curve by integrating over time using the Sound Intensity vs. Flow Rate curve for distance r=30 cm. The corresponding flow rate in liters per second (LPS) is determined by dividing the corresponding flow rate in LPM by 60 seconds. The volume of air inhaled or exhaled may then be calculated by, for example, averaging consecutive flow-rates over the time interval. For example, at time t=0 s, the volume of air is 0. Then at the end of 0.5 s, the beginning and end flow rates (0 and 0.40 LPS) may be averaged to determine a volume of air of 0.20 LPS at t=0.5 s. Additionally, or alternatively, the volume of air inhaled or exhaled may be determined by multiplying a flow rate (in LPS) for a time interval by a duration of the time interval (in this instance, 0.5 seconds) to determine the volume of air inhaled or exhaled in liters (L) for each time interval. The volume of air inhaled or exhaled in liters (L) for each time interval are then added together to determine the lung capacity of the user in liters.

TABLE 3

| Time (s) | Sound Intensity (dB) for User X | Corresponding Flow Rate (LPM) | Corresponding Flow Rate (LPS) | Volume of Air Inhaled or Exhaled (L) for User X |
|---|---|---|---|---|
| 0 | 74 | 24 | 0.400 | 0.00 |
| 0.5 | 74 | 24 | 0.400 | 0.20 |
| 1 | 74 | 24 | 0.400 | 0.20 |
| 1.5 | 74 | 24 | 0.400 | 0.20 |
| 2 | 69 | 22 | 0.367 | 0.19 |
| 2.5 | 69 | 22 | 0.367 | 0.18 |
| 3 | 81 | 28 | 0.467 | 0.21 |
| 3.5 | 81 | 28 | 0.467 | 0.23 |
| 4 | 84 | 32 | 0.533 | 0.25 |
| 4.5 | 84 | 32 | 0.533 | 0.27 |
| 5 | 45 | 16 | 0.267 | 0.20 |
| 5.5 | 45 | 16 | 0.267 | 0.13 |
| 6 | 0 | 0 | 0.000 | 0.07 |
| Total volume inhaled or exhaled (L) (lung capacity) for User X | | | | 2.33 |

Optionally, in some embodiments, a peak air flow rate of the sound recording may be determined (step 730). This determination may be made by determining the highest sound intensity value of the sound recording and determining the air flow volume corresponding the highest sound intensity and/or selecting the highest air flow volume value from a plurality of determined air flow volumes. For User X, the peak air flow volume is 32 LPM, which corresponds to a sound intensity value of 84 dB.

Figure 8A:
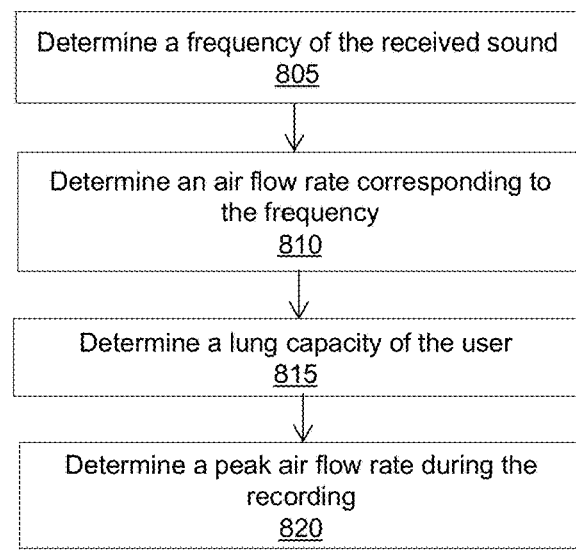
FIG. 8A is a flowchart depicting a process for determining a lung capacity of a user and/or a peak air flow rate of inhalation and/or exhalation of a user, consistent with some embodiments of the present invention.

FIG. 8A is a flowchart depicting a process 800 for executing step 615, determining a lung capacity of a user and/or a peak air flow rate of inhalation and/or exhalation of a user. Process 800 may be executed by a system like system 100 and/or a component or combination of components thereof. Process 800 makes use of a sound-producing breathing device that emits sound of a particular frequency responsively to a flow rate of air through the sound-producing breathing device.

Initially, in step 805, a frequency, or range of frequencies, of the sound for each interval (e.g., 1 second, 0.5 seconds, 0.1 seconds, etc.) in the sound recording may be determined. The frequency of sound for each interval may then be used to determine an air flow rate for each interval (step 810) using, for example, a table correlating sound frequency with air flow rates. An example of such a table is provided by Table 4, reproduced below.

TABLE 4

| Flow Rate (LPM) | Sound Frequency (Hz) |
|---|---|
| 0 | 0 |
| 2 | 262 |
| 4 | 277 |
| 6 | 294 |
| 8 | 311 |
| 10 | 330 |
| 12 | 349 |
| 14 | 370 |
| 16 | 392 |
| 18 | 415 |
| 20 | 440 |
| 22 | 466 |
| 24 | 494 |
| 26 | 524 |
| 28 | 556 |
| 30 | 589 |
| 32 | 623 |
| 34 | 650 |
| 36 | 0 |
| 38 | 0 |
| 40 | 0 |

The determined flow rates for each interval may then be used to determine a volume of air inhaled or exhaled during each interval, which corresponds to the user's lung capacity for the respective interval. The values of lung capacity for each interval may then be added together to determine an overall lung capacity for the user (step 815). Table 5 provides experimentally measured data for a user Y where a sound frequency for each time interval is determined via execution of step 805.

TABLE 5

| Time (s) | Sound Frequency (Hz) Recorded for User Y |
|---|---|
| 0 | 494 |
| 0.5 | 494 |
| 1 | 494 |
| 1.5 | 494 |
| 2 | 466 |
| 2.5 | 466 |
| 3 | 556 |
| 3.5 | 556 |
| 4 | 623 |
| 4.5 | 623 |
| 5 | 392 |
| 5.5 | 392 |
| 6 | 0 |

Figure 8B:
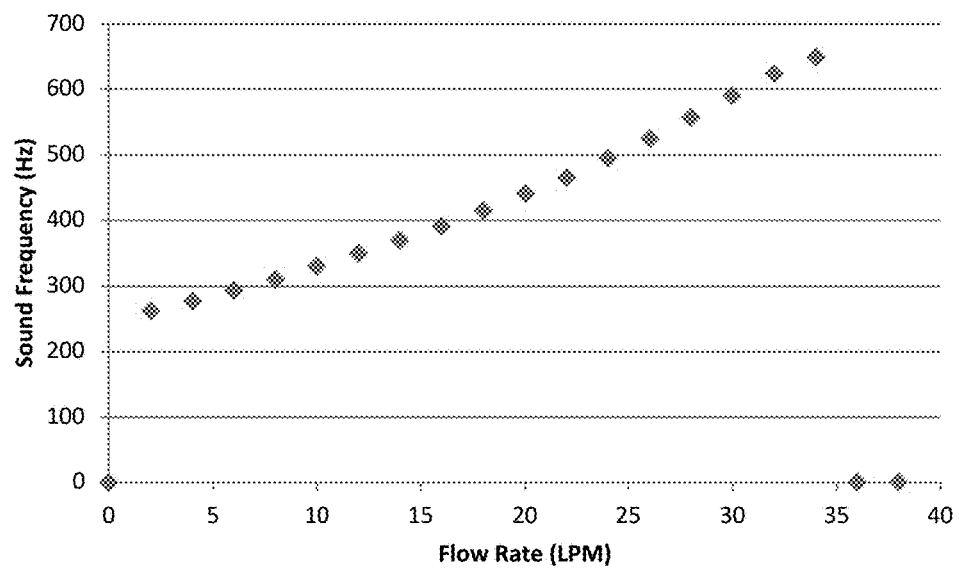
FIG. 8B depicts a graph plotting sound frequency as a function of air flow rate, consistent with some embodiments of the present invention.
Figure 8C:
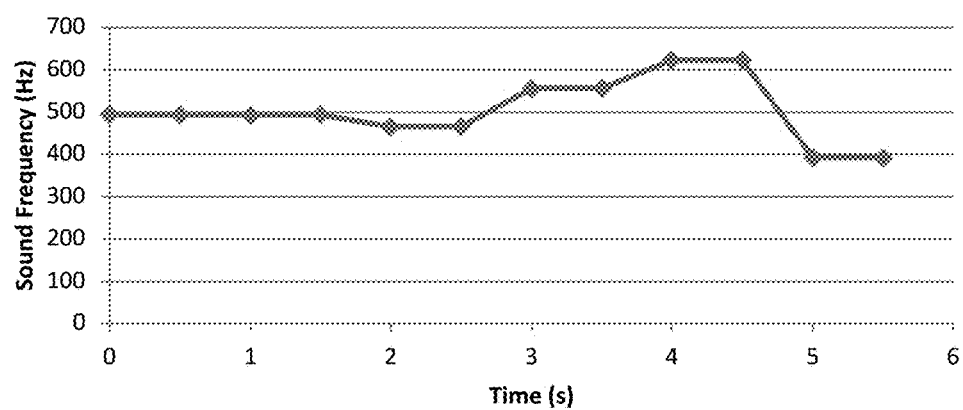
FIG. 8C depicts a graph plotting sound frequency as a function of time for a User Y, consistent with some embodiments of the present invention.

A plot of the data in Table 5 is provided by graph 801 shown in FIG. 8B. These determined frequencies may then be correlated with their associated air flow rates in LPM, which may then be converted into LPS as shown in Table 6, below. Then, the volume of air inhaled or exhaled for each time interval may be determined. In some embodiments, the volume of air inhaled or exhaled may be calculated by, for example, averaging consecutive flow-rates over the time interval. For example, at time t=0 s, the volume of air is 0. Then at the end of 0.5 s, the beginning and end flow rates (0 and 0.40 LPS) may be averaged to determine a volume of air of 0.20 LPS at t=0.5 s. Additionally, or alternatively, the volume of air inhaled or exhaled may be determined by multiplying a flow rate (in LPS) for a time interval by the duration of the time interval (in this instance 5 s).

These volumes may then be added together to determine a user's lung capacity over the duration of the recording, which in this example is 2.52 L.

TABLE 6

| Time (s) | Sound Frequency (Hz) Recorded for User Y | Corresponding Flow Rate (LPM) | Corresponding Flow Rate (LPS) | Volume Inhaled or Exhaled (L) by User Y |
|---|---|---|---|---|
| 0 | 494 | 24 | 0.400 | 0.00 |
| 0.5 | 494 | 24 | 0.400 | 0.20 |
| 1 | 494 | 24 | 0.400 | 0.20 |
| 1.5 | 494 | 24 | 0.400 | 0.20 |
| 2 | 466 | 33 | 0.550 | 0.24 |
| 2.5 | 466 | 33 | 0.550 | 0.28 |
| 3 | 556 | 28 | 0.467 | 0.25 |
| 3.5 | 556 | 28 | 0.467 | 0.23 |

TABLE 6-continued

| Time (s) | Sound Frequency (Hz) Recorded for User Y | Corresponding Flow Rate (LPM) | Corresponding Flow Rate (LPS) | Volume Inhaled or Exhaled (L) by User Y |
|---|---|---|---|---|
| 4 | 623 | 32 | 0.533 | 0.25 |
| 4.5 | 623 | 32 | 0.533 | 0.27 |
| 5 | 392 | 16 | 0.267 | 0.20 |
| 5.5 | 392 | 16 | 0.267 | 0.13 |
| 6 | 0 | 0 | 0.000 | 0.07 |
| Total volume of air inhaled or exhaled by User Y | | | | 2.52 |

Figure 10A:
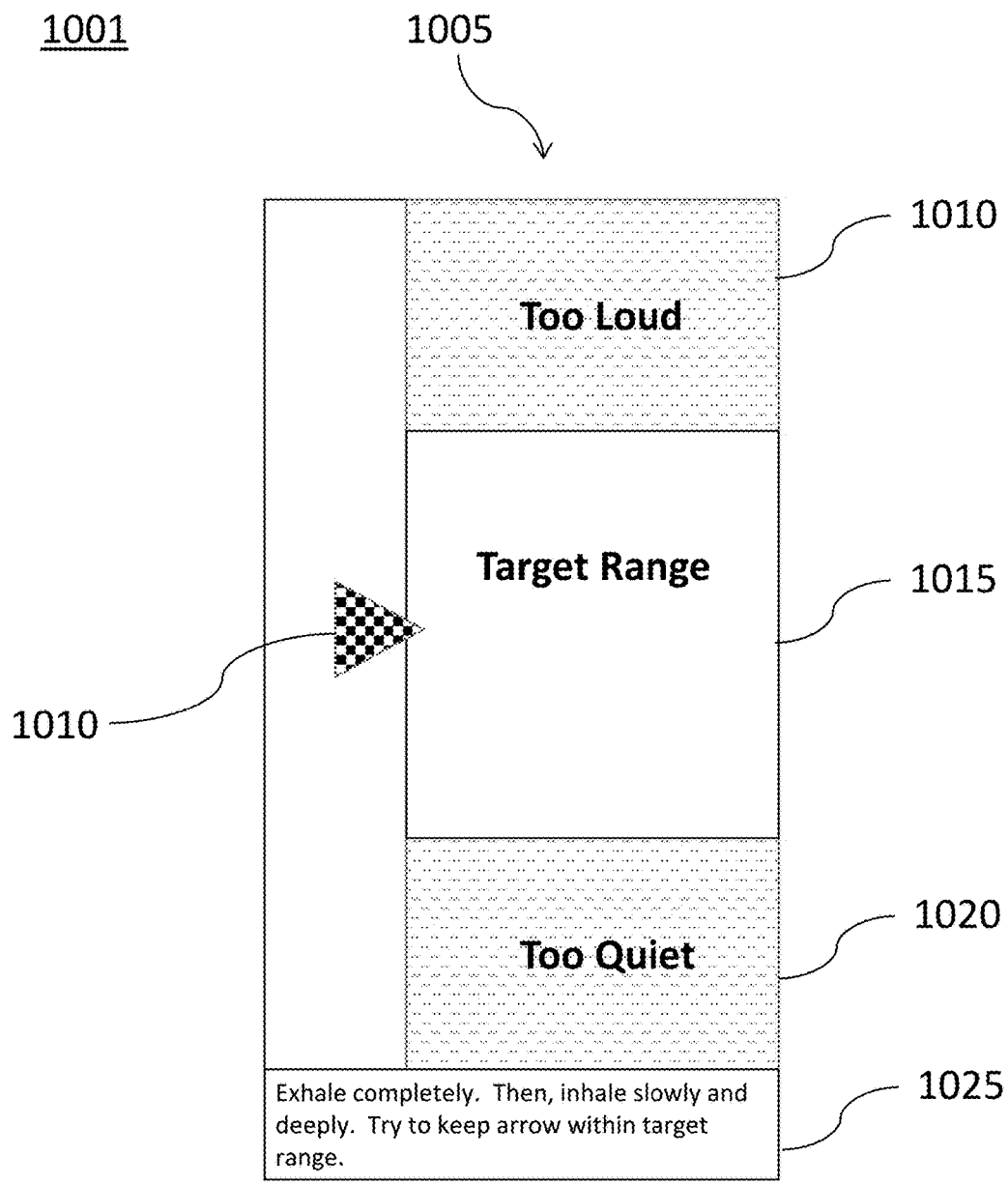
FIGS. 10A-10D provide exemplary interfaces by which a user may use a sound-producing breathing device and make a sound recording, consistent with some embodiments of the present invention.

FIGS. 10A-10E provide screen captures of user interface 1001, 1002, 1003, 1004, and 1005, respectively. User interfaces 1001 and 1002 correspond with processes 500, 600, and/or 700; user interfaces 1001 and 1002 correspond with processes 500, 600, and/or 800, and user interface 1005 corresponds with processes 500, 600, 700, and/or 800. User interface 1001 includes a sound intensity bar graph 1005 that graphically depicts a range of sound intensities that are too quiet (which may correspond with an air flow rate that is below a target range) 1020, a range of sound intensities that are too large (which may correspond with an air flow rate that is above the target range) 1010, and a target range (which may correspond with an air flow rate that at the target range) 1015. Interface 1001 may also include a sound intensity indicator 1010, which graphically represents whether the sound intensity produced by the user using the sound-producing breathing device is too loud, too quiet, or within the target range. Interface 1001 further includes a message window 1025 that may, for example, provide a user with instructions for using the sound-producing breathing device. In the embodiment of FIG. 10A, the message shown in message window 1025 is "Exhale completely. Then, inhale slowly and deeply. Try to keep the arrow within the target range."

Figure 10B:
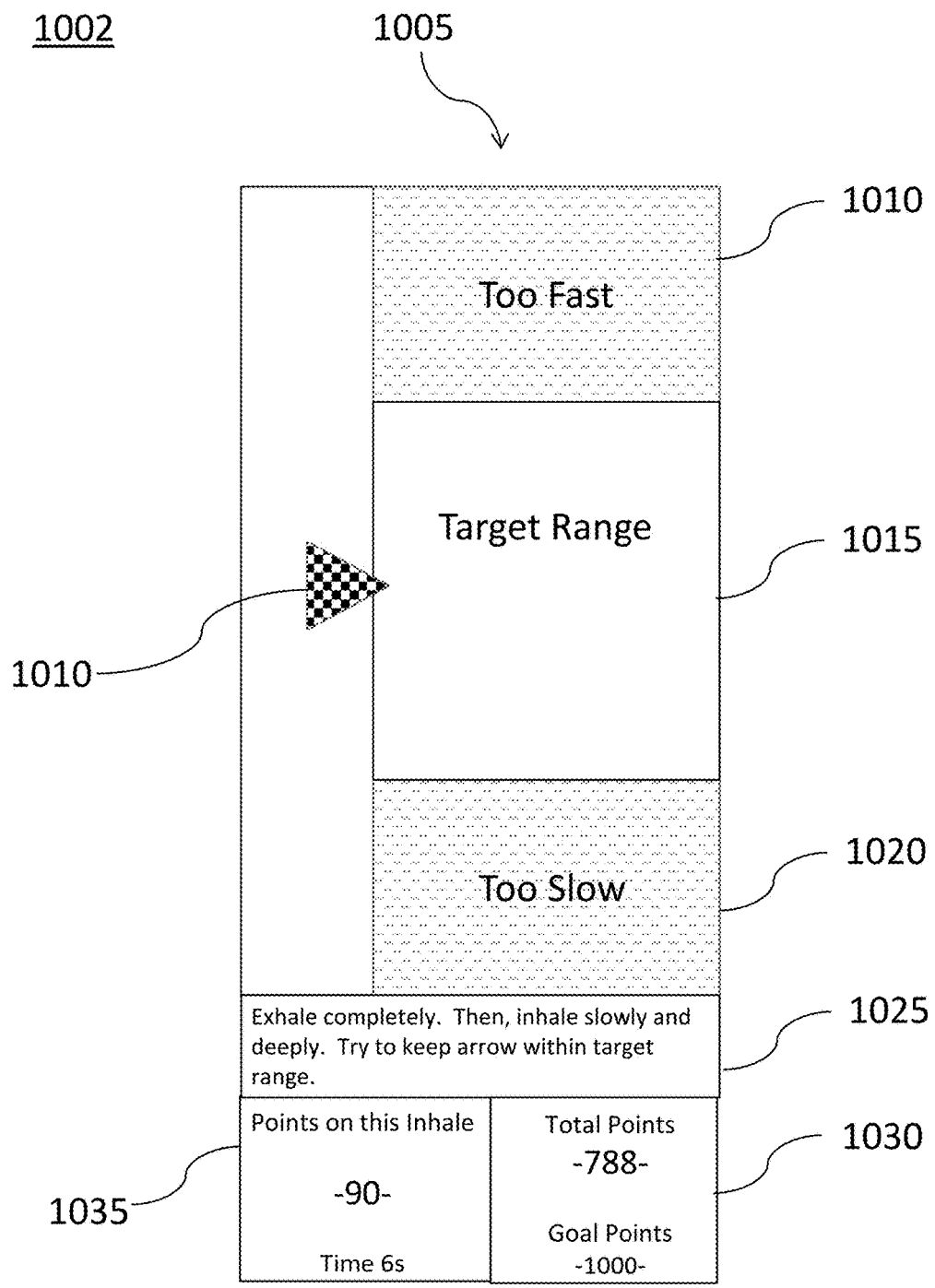

User interface 1002 of FIG. 10B is substantially similar to user interface 1001 with the exception that user interface 1002 further includes a first feedback window 1035 and a second feedback window 1030. Feedback windows 1030 and 1035 provide the user with feedback regarding how well they are doing with performance of their breathing exercises and whether or not they are on track with their breathing exercise routine. Provision of feedback within feedback windows 1030 and 1035 may be representations of the indication provided in step 645. In some instances, the feedback provided within feedback windows 1030 and 1035 may be points awarded for a particular inhalation or exhalation period, total points awarded as measured over a day, a week, a month, etc., and a number of goal points. The award of points to a user for using the sound-producing breathing device 140 may be an attempt to incentivize user to perform his or her breathing exercises or otherwise gamify the performance of breathing exercises. In the embodiment of the FIG. 10B, the user has been awarded 90 points for a sound recording associated with a 6 s interval and this information is provided in feedback window 1035.

Figure 10C:
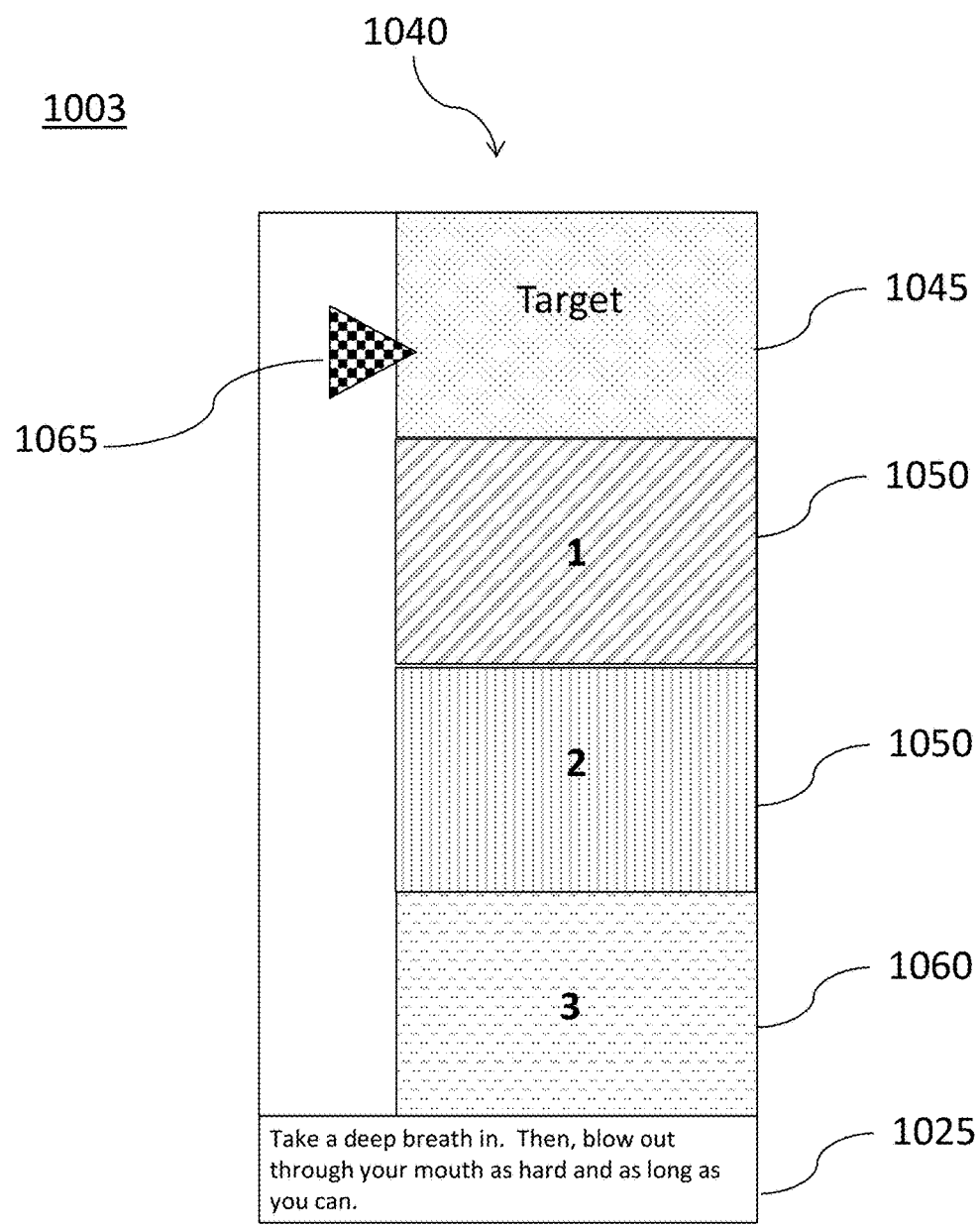

User interface 1003 of FIG. 10C includes a frequency bar graph 1040 that graphically depicts a range of sound frequencies that have differing degrees of being below a target frequency. In bar graph 1040, depictions of the frequency ranges are ranked so that there are depictions of a target range 1045, a range one degree below the target range 1050, a range two degrees below the target range, and a range three degrees below the target range. How many frequencies are encompassed within a range may vary based on the sound-producing breathing device being used by exemplary ranges include but are not limited to 50, 75, 100, or 125 Hz. In one embodiment where the target range is 600 Hz, a first degree below 600 Hz may be 550 Hz, a second degree below 600 Hz may be 500 Hz, and a third degree below 600 Hz may be 550 Hz.

Interface 1001 may also include a sound frequency indicator 1065, which graphically represents whether the sound frequency produced by the user using the sound-producing breathing device is within the target range. Interface 1001 further includes a message window. In the embodiment of FIG. 10B, the message shown in message window 1025 is "Take a deep breath in. Then, blow out through your mouth as hard and as long as you can."

Figure 10D:
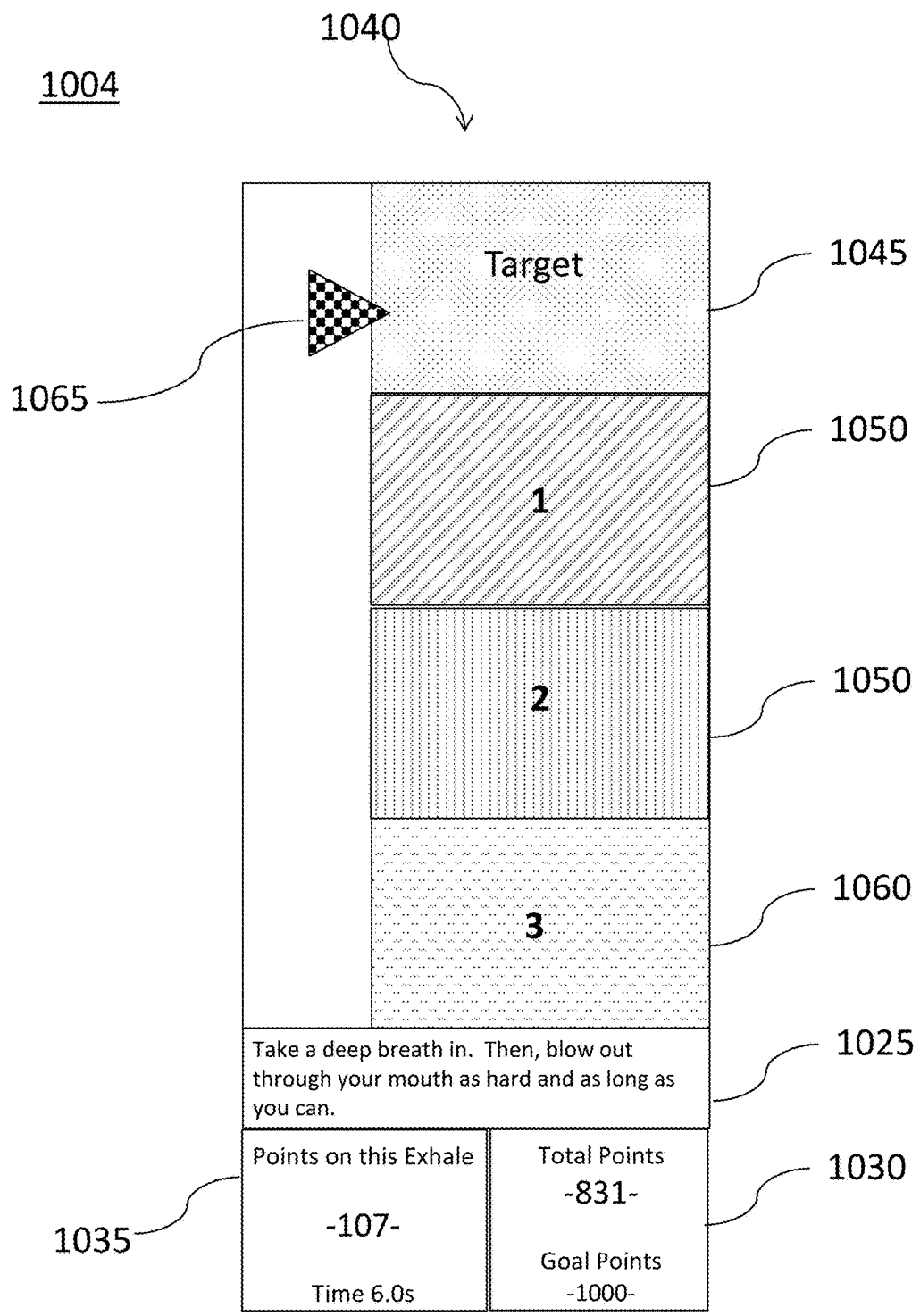

User interface 1004 of FIG. 10D is substantially similar to user interface 1003 with the exception that user interface 1004 further includes a first feedback window 1035 and a second feedback window 1030.

In some instances, user interfaces 1001, 1002, 1003, and/or 10014 may be provided to the user via, for example, a display like display 312 while the user is using the sound-producing breathing device and/or making a sound recording using the sound-producing breathing device. In this way, the user may receive instantaneous feedback about their performance of the breathing exercise. At times, movement of sound intensity indicator 1010 and/or frequency indicator 1065 may be representations of the indication provided in step 645.

The target ranges for bar graphs 1005 and/or 1040 may be standard target ranges that may, in some instances, be specific to a sound-producing breathing device being used, a correlation table or set of correlation tables being used, and/or may be specific to particular user. In some instances, the target ranges may be set by, for example, process 500 and/or execution of step(s) 510, 515, 530, and/or 555.

FIG. 10E provides an exemplary user-monitoring portal interface 1005 that may be provided by the web application and/or software/mobile application running on the user electronic device 125. The user-monitoring portal interface 1005 may be displayed to a user and/or a treatment provider and may include user-identifying information, one or more options for a time period (week, month, year) over which data is to be viewed, and statistics analysis of sound recordings. In the embodiment of FIG. 10E, the time period being viewed is the previous week (i.e., "last week"). Exemplary statistics that may be provided by user interface 1005 include, but are not limited to, the average number of daily uses, average volume of exhaled air/lung capacity, peak exhale volume over all sound recordings for the time interval selected, average exhale volume/lung capacity, average exhale duration, peak exhalation flow rate, average exhalation flow rate, average volume of inhaled air/lung capacity, peak inhale volume over all sound recordings for the time interval selected, average inhale volume/lung capacity, average inhale duration, peak inhalation flow rate, and average inhalation flow rate.

We claim:

1. A method for determining a lung capacity of a user comprising:
receiving, by the processor, a distance between the sound-producing breathing device and the microphone;
receiving, by a processor, a recording of sound produced by a sound-producing breathing apparatus when a user inhales or exhales through the sound-producing breathing apparatus, the recording being made with a microphone resident within a user electronic device operated by the user, the microphone being communicatively coupled to the processor;

determining, by the processor, an intensity of the sound included in the received sound recording;

determining, by the processor, a lung capacity of the user responsively to the received distance and determined intensity; and facilitating, by the processor, provision of an indication of the lung capacity to at least one of the user and a caregiver for the user.

2. The method of claim 1, wherein the sound recording is divided into a plurality of time intervals and a sound intensity is determined for each time interval, the determining of the lung capacity of the user comprising:

accessing, by the processor, a correlation table stored in a database communicatively coupled to the processor, the correlation table correlating sound intensity and air flow rates for the sound-producing breathing device and being specific to the distance between the sound-producing breathing device and the microphone and the type of sound-producing breathing device used to make the sound recording;

determining, by the processor, an air flow rate corresponding to the intensity for each time interval using the correlation table;

determining, by the processor, a volume of air inhaled or exhaled for each time interval; and determining, by the processor, a total volume of air inhaled or exhaled for all the time intervals included in the plurality of time intervals.

3. The method of claim 1, wherein the sound recording is divided into a plurality of time intervals and a sound intensity is determined for each time interval, the determining of the lung capacity of the user comprising:

determining, by the processor, whether a correlation table correlating sound intensity and air flow rates for the sound-producing breathing device at the distance is available and, if not, generating the correlation table that correlates sound intensity and air flow rates for the sound-producing breathing device at the distance;

accessing, by the processor, the correlation table;

determining, by the processor, the air flow rate corresponding to the intensity for each time interval using the correlation table;

determining, by the processor, a volume of air inhaled or exhaled for each time interval; and determining, by the processor, a total volume of air inhaled or exhaled for all the time intervals included in the plurality of time intervals.

4. The method of claim 1, wherein the sound recording is divided into a plurality of time intervals and a sound intensity is determined for each time interval, the determining of the lung capacity of the user comprising:

determining, by the processor, a relationship between the each of the determined sound intensities and an air flow rate for the sound-producing breathing device at the distance;

determining, by the processor, a volume of air inhaled or exhaled for each time interval using the air flow rate using the relationship; and determining, by the processor, a total volume of air inhaled or exhaled for all the time intervals included in the plurality of time intervals using the volume of air inhaled or exhaled for each time interval.

5. The method of claim 1, further comprising:
communicating, by the processor, the lung capacity to a third-party computer system.

6. The method of claim 1, further comprising:
determining, by the processor, whether the lung capacity falls below a threshold value and, if so, determining that an intervention is required and executing the intervention.

7. The method of claim 1, further comprising:
determining, by the processor, a peak air flow rate for the sound recording.

8. The method of claim 1, further comprising:
receiving, by the processor, a goal for the user's lung capacity;
determining, by the processor, how the determined lung capacity compares to the goal; and
facilitating, by the processor, provision of an indication of the comparison to the user.

9. A method for determining a lung capacity of a user comprising:
receiving, by a processor, a distance between the sound-producing breathing device and the microphone;
receiving, by the processor, a recording of sound produced by the sound-producing breathing apparatus when a user inhales or exhales through the sound-producing breathing apparatus, the recording being made with a microphone resident within a user electronic device operated by the user and communicatively coupled to the processor;
determining, by the processor, a frequency of the sound included in the received sound recording;
determining, by the processor, a lung capacity of the user responsively to the received distance and the determined frequency; and
facilitating, by the processor, provision of an indication of the lung capacity to the user.

10. The method of claim 9, wherein the sound recording is divided into a plurality of time intervals and a sound frequency is determined for each time interval, the determining of the lung capacity of the user comprising:
accessing, by the processor, a correlation table stored in a database communicatively coupled to the processor, the correlation table correlating sound frequency and air flow rates for the sound-producing breathing device;
determining, by the processor, an air flow rate corresponding to the sound frequency for each time interval using the correlation table;
determining, by the processor, a volume of air inhaled or exhaled for each time interval; and
determining, by the processor, a total volume of air inhaled or exhaled for all the time intervals included in the plurality of time intervals.

11. The method of claim 10, wherein the correlation table is specific to the type of sound-producing breathing device used to make the sound recording.

12. The method of claim 9, wherein the sound recording is divided into a plurality of time intervals and a sound frequency is determined for each time interval, the determining of the lung capacity of the user comprising:
determining, by the processor, a relationship between the each of the determined sound frequencies and an air flow rate for the sound-producing breathing device;
determining, by the processor, a volume of air inhaled or exhaled for each time interval using the air flow rate using the relationship; and
determining, by the processor, a total volume of air inhaled or exhaled for all the time intervals included in the plurality of time intervals using the volume of air inhaled or exhaled for each time interval.

13. The method of claim 9, further comprising:
determining, by the processor, a peak air flow rate for the sound recording.

14. The method of claim 9, further comprising:
receiving, by the processor, a goal for the user's lung capacity;
determining, by the processor, how the determined lung capacity compares to the goal; and
facilitating, by the processor, provision of an indication of the comparison to the user.

15. A system for determining a lung capacity of a user comprising:
a sound-producing breathing apparatus; and
a processor communicatively coupled to a microphone, the processor having a set of instructions stored thereon which when executed by the processor cause the processor to:
receive a distance between the sound-producing breathing device and the microphone;
receive a recording of sound produced by the sound-producing breathing apparatus when a user inhales or exhales through the sound-producing breathing apparatus, the recording being made with a microphone resident within a user electronic device operated by the user and communicatively coupled to the processor;
determine an intensity of the sound included in the received sound recording;
determine a lung capacity of the user responsively to the received distance and determined intensity; and
facilitate provision of an indication of the lung capacity to the user.

16. The system of claim 15, further comprising:
a third-party computer system communicatively coupled to the processor and configured to receive the indication.

17. The system of claim 15, further comprising:
an apparatus configured to maintain a consistent distance between the sound-producing apparatus and the microphone while the user is using the sound-producing apparatus to generate a sound.

18. The system of claim 15, wherein the processor is housed in a user electronic device that includes a display device and the set of instructions stored on the processor, which when executed by the processor further cause the processor to:
provide a message to the user regarding at least one of instructions for using the sound-producing breathing apparatus and an indication of their lung capacity.

* * * * *